(12) United States Patent
Stuebe et al.

(10) Patent No.: US 7,818,155 B2
(45) Date of Patent: Oct. 19, 2010

(54) ESOPHAGEAL WAVEFORM ANALYSIS FOR DETECTION AND QUANTIFICATION OF REFLUX EPISODES

(75) Inventors: Thomas D. Stuebe, Littleton, CO (US); Venkatachalam Chandrasekar, Fort Collins, CO (US); Awad Al-Zaben, Irbid (JO)

(73) Assignee: Sandhill Scientific, Inc., Highlands Ranch, CO (US)

( * ) Notice: Subject to any disclaimer, the term of this patent is extended or adjusted under 35 U.S.C. 154(b) by 28 days.

(21) Appl. No.: 12/029,461

(22) Filed: Feb. 11, 2008

(65) Prior Publication Data

US 2008/0306411 A1 Dec. 11, 2008

Related U.S. Application Data

(63) Continuation of application No. 10/935,896, filed on Sep. 7, 2004, now abandoned.

(51) Int. Cl.
*G06G 7/58* (2006.01)
(52) U.S. Cl. ......................................... 703/11
(58) Field of Classification Search .................... 703/11
See application file for complete search history.

(56) References Cited

U.S. PATENT DOCUMENTS 5,109,870 A  5/1992  Silny et al.

OTHER PUBLICATIONS

Al-Zaben et al., "Thresholding Reflux Episodes in Impedance Measurements Using a Neuro-Fuzzy System", Biomedical Sciences Instrumentation, Apr. 2002, pp. 263-265, vol. 38, ISA.

26th Annual Meeting of the European Society of Pediatric Gastroenterology and Nutrition, Gothenburg, Sweden Jun. 27-30, 1993. Abstracts Published by Raven Press vol. 17.

S.Shay et al., "Acid Rereflux: A Review, Emphasizing Detection by Impedance, Manometry and Scintigraphy . . . ", Digestive Diseases and Sciences, vol. 48, No. 1, Jan. 2003; pp. 1-9.

D. Sifrim et al., "Acid, Non-Acid, and Gas Reflux in Patients With Gastroesophageal Reflux Disease During Ambulatory 24-Hour pH-Impedance Recordings", American Journal of Gastroenterology 2001:120; pp. 1588-1598.

M.F.Vela et al., "Baclofen Decreases Acid and Non-acid Postprandial Gastroesophageal Reflux Measured by Combined Multichannel . . . ", Alimentary Pharmacology Therapy 2003:17; pp. 243-251.

(Continued)

*Primary Examiner*—Hugh Jones
(74) *Attorney, Agent, or Firm*—James R. Young; Cochran Freund & Young LLC

(57) ABSTRACT

A system and method for automatically analyzing impedance and pH data from an esophageal probe includes a data collection system that collects and stores the output from the sensors for a certain period of time to locate reflux episodes in the waveforms. The data analysis system uses wavelet analysis to assist in locating bolus entry and exit points in the waveforms and to smooth waveforms for additional analysis. It also distinguishes between candidate acid reflux episodes and candidate non-acid reflux episodes for determining actual acid reflux episodes and non-acid reflux episodes, and it distinguishes between, and provides different signal processing for, signals from patients that have healthy esophageal tissue and those that have diseased esophageal tissue.

26 Claims, 11 Drawing Sheets

OTHER PUBLICATIONS

D. Sifrim et al., "Composition of the Postprandial Refluxate in Patients With Gastroesophageal Reflux Disease", The American Journal of Gastroenterology; vol. 96, No. 3, 2001; pp. 647-655.

T. Wenzl et al., "Esophageal pH Monitoring and Impedance Measurement: A Comparison of Two Diagnostic Tests for Gastroesophageal Reflux", Journal of Pediatric Gastroenterology and Nutrition; vol. 34, 2002; pp. 519-523.

T. Wenzl, "Evaluation of Gastroesophageal Reflux Events in Children Using Multichannel Intraluminal Electrical Impedance", The American Journal of Medicine; vol. 115 (3A), 2003; pp. 161S-165S.

C.S. Peter et al., "Gastroesophageal Reflux and Apnea of Prematurity: No Temporal Relationship", Pediatrics; vol. 109, No. 1, Jan. 2002; pp. 8-11.

T. G. Wenzl et al., "Association of Apnea and Nonacid Gastroesophageal Reflux in Infants: Investigations with the Intraluminal Impedance Technique", Pediatric Pulmonology, vol. 31, 2001; pp. 144-149.

C.S. Peter et al., "Influence of Nasogastric Tubes on Gastroesophageal Reflux in Preterm Infants: A Multiple intraluminal Impedance Study", Journal of Pediatrics, vol. 141, 2002; pp. 227-229.

T. G. Wenzl et al., "Intraluminal Impedance: An Ideal Technique For Evaluating Pediatric Gastroesophageal Reflux Disease", Current Gastroenterology Reports, vol. 2, 2000; pp. 259-264.

T.G. Wenzl, "Investigating Esophageal Reflux with the Intraluminal Impedance Technique", Journal of Pediatric Gastroenterology and Nutrition, vol. 34, 2002; pp. 261-268.

S. Shay et al., "Multichannel Intraluminal Impedance Accurately Detects Fast, Recumbent Reflux Events and Their Clearing", American Journal of Physiology-Gastrointestinal & Liver Physiology, vol. 10, Apr. 2002; pp. G376-G383.

R. Tutuian et al., Multichannel Intraluminal Impedance in Esophageal Function Testing and Gastroesophageal Reflux Monitoring, Journal of Clinical Gastroenterology, vol. 37, No. 3, 2003; pp. 206-215.

H.N. Nguyen et al., "Multiple Intraluminal Electrical Impedancometry for Recording of Upper GI Motility", The American Journal of Gastroenterology; vol. 94; No. 2, 1999; pp. 1-11.

R. Tutuian et al., "Use of Multichannel Intraluminal Impedance to Document Proximal Esophageal and Pharynegeal Nonacidic Reflux Episodes", The American Journal of Medicine, vol. 115:(3A), 2003; pp. 119S-123S.

D. Sifrim et al., "Patterns of Gas and Liquid Reflux During Transient Lower Oesophageal Sphincter Relaxation: A Study Using Intraluminal Electrical Impedance", Gut, vol. 44, Jul. 1998; pp. 47-54.

N.S. Balaji et al., "Redefining Gastroesophageal Reflux (GER): Detection Using Multichannel Intraluminal Impedance in Healthy Volunteers", Surgical Endoscopy, (2003); pp. 1-8.

M. Vela et al., "Simultaneous Intraesophageal Impedance and pH Measurement of Acid and Nonacid Reflux: Effect of Omeprazole", Gastroenterology, vol. 120, 2001; pp. 1599-1606.

J. Silny, "Intraluminal Multiple Electric Impedance Procedure for Measurement of Gastrointestinal Motility", Helmholtz-Institute for Biomedical Engineering, Univ of Tech., Aachen, Germany, 1991; pp. 151-162.

A. Al-Zaben et al., "Detection of Gastrointestinal Tract Events from Multichannel Intraluminal Impedance Measurements", 38th Annual Rocky Mountain Bioengr. Symposium, vol. 37, 2001; pp. 55-61.

Trachterna et al., "Procedure For The Semi-Automatic Detection of Gatro-Oesophageal Reflux Patterns in Intraluminal Impedance Measurements in Infants", Medical Engineering & Physics, vol. 21, 1999; pp. 195-201.

LIQUID REFLUX EPISODE

LIQUID REFLUX EPISODE AND SWALLOW

ESOPHAGEAL WAVEFORM ANALYSIS FOR DETECTION AND QUANTIFICATION OF REFLUX EPISODES

CROSS REFERENCE TO RELATED APPLICATIONS

This application claims the benefit of U.S. Provisional Patent Application 60/500,555 entitled "Esophageal Waveform Analysis for Detection and Quantification of Reflux Episodes", filed Sep. 5, 2003, by Thomas D. Stuebe, and U.S. Provisional Application 60/554,794 entitled "Intraluminal Impedance: Electromagnetic Modeling, Signal Analysis, and Computer-Assisted Diagnosis of Gastroespohageal Reflux", filed Mar. 19, 2004, by Awad Al-Zaben, Venkatachalam Chandrasekar, and Thomas D. Stuebe, and the entire contents of both applications are hereby specifically incorporated by reference herein for all they disclose and teach.

BACKGROUND OF THE INVENTION

1. Field of the Invention

The present invention relates generally to gastroesophageal reflux diagnostic systems, and more particularly to automated system for processing impedance and pH signals from an esophageal monitoring device to locate bolus entry and exit points on an impedance waveform and to locate retrograde bolus movement episodes across impedance channel waveforms.

2. Description of the Background

Gastrointestinal reflux is the movement of liquids, which may, but do not necessarily, include stomach acids, upwardly in the esophagus, i.e., away from the stomach instead of toward the stomach. The esophagus, which extends from a person's or animal's pharynx to the stomach, normally functions to transport food and liquids downwardly from the pharynx to the stomach during a swallow. During a normal swallow, a peristaltic wave (i.e., a contraction of the muscles of the esophagus) begins at the upper end of the esophagus and moves progressively downward in the esophagus and works to push the food or liquid downwardly to the Lower Esophageal Sphincter (LES), which opens and allows the food or liquid to enter the stomach. The LES, which is a circular or ring-like muscle structure, normally prevents the contents of the stomach from re-entering the esophagus. Therefore, in a normal swallow, the esophageal muscles and the LES work in conjunction with each other to transport liquid or food to the stomach and to prevent retrograde movement of the food or liquid in the opposite direction.

Gastrointestinal reflux, or Gastroesophageal reflux disease (GERD), is an abnormal esophageal condition or function in which a portion of the stomach contents passes in a reverse direction through the LES and moves at least some distance upwardly into the esophagus in a retrograde motion. In persons with GERD, the LES muscle may be weak or may relax inappropriately with exposure to fatty and spicy foods, certain types of medications, tight clothing, smoking, drinking alcohol, vigorous exercise, or changes in body position. The reflux can cause problems, such as heartburn-like pain symptoms, chest pain similar to cardiac problems, aggravated asthma symptoms, hoarseness, sinus problems, snoring problems, and other respiratory problems. Severe or prolonged acid reflux can cause inflammation (esophagitis) and can ultimately damage the lining of the esophagus. Reflux is usually not noticeable or harmful during the day, since the esophagus is protected during waking hours by swallowing, by the flow of saliva, and by gravity (assuming the sufferer is standing or sitting up). However, at night, these protective mechanisms are less effective. Consequently, nighttime acid reflux is more likely to remain in the esophagus longer and can cause greater damage.

A normal course of treatment for non-critical reflux is typically the administration of acid-reducing or acid-blocking medications. However, serious and/or long-term gastrointestinal reflux can often necessitate surgery to the LES or to the stomach. Therefore, it is desirable in all cases to be able to detect, measure, and diagnose any abnormal operations of the esophagus in order to prevent or treat the reflux.

One fairly common method of detecting the occurrence of gastrointestinal reflux has been to insert a probe with a pH-sensitive billet into the esophagus of a subject to measure acid or pH levels. For example, one or more antimony billets have been used to detect hydrochloric acid (HCl) as a marker for acid reflux. When the probe in the esophagus detects a drop in pH levels, it is assumed that gastric contents containing HCl have entered the esophagus from the stomach. Consequently, the occurrence of a pH value below about 4.0 is commonly held to indicate a reflux episode. The value of 4.0 pH is commonly used because the esophagus has a typical pH of approximately 6.0 and the stomach has a typical pH of approximately 4.0. The value of 4.0 is commonly held to be the lowest pH level tolerable in the esophagus without causing caustic damage to the esophageal lining.

One drawback of that pH-detecting approach is that acid control medication defeats the ability to detect acid reflux. The HCl acid may not be sufficiently present to be used as a marker for reflux episodes. Another drawback of this approach is that it does not show the operational dynamics of the esophagus, i.e., it does not show bolus movement. (The word "bolus" is used herein as a convenient term to denote any quantity of solid and/or liquid material moving through the esophagus in either direction and is not necessarily limited to a small, round mass.) Consequently, this prior art approach cannot determine the underlying cause of the reflux. In addition, this approach may not be able to continuously measure acid levels in a patient over a significant period of time. Furthermore, it may not show the extent or duration of a reflux occurrence, as the prior art approach is incapable of detecting the reflux of relatively non-acidic stomach fluids, i.e., a "non-acid" reflux.

A more recent development in esophageal monitoring has included the use of a probe to measure electric impedance in the esophagus, such as the probe described in the U.S. Pat. No. 5,109,870 issued to J. Silny et al., which is incorporated herein by reference. Essentially, such impedance probes can sense electric impedances and changes in electric impedances at one or more locations in the esophagus above the LES, including such changes in impedance caused by reflux of stomach contents into the esophagus.

Changes in pH and/or impedance from such esophageal measurements are typically presented as raw numbers or line graphs that show values taken over time. Therefore, a physician or other medical personnel has to interpret the data, i.e., numbers or values from the graphs, in order to obtain meaningful information, such as occurrences of reflux episodes and start and stop times of such episodes. Such interpretations are difficult and time consuming. It is even more difficult if the analyzing person has to correlate multiple data readings for a patient, and it is not unusual for such manual analysis of typical 24-hour gastroesophageal reflux monitoring studies to require up to 4 hours of an experienced clinician's time. This time requirement to discern and extract meaningful information from such pH and/or impedance measurements is significant enough that it is a substantial impediment to use such esophageal impedance data beyond academic interest and research settings. Also, the mental challenge of interpreting impedance waveforms for retrograde bolus movement episodes is enough so that mental fatigue can cause human scoring to degrade over the course of the study.

Therefore, there remains a need for improvements in the detection and analysis of esophageal reflux from impedance and/or pH measurements in the esophagus.

SUMMARY OF THE INVENTION

Accordingly, it is a general object of the present invention to provide a system that can assist a health care professional in identifying possible indications of occurrences of reflux episodes in data obtained from impedance measurements in a test subject's esophagus. A more specific object of the invention is to provide a method of locating possible bolus entry and bolus exit points on an impedance waveform. Another specific object of the invention is to provide a method of locating retrograte movement episodes across impedance channel waveforms.

The present invention overcomes the disadvantages and limitations of previous solutions by providing a system and method for automatically analyzing data from an esophageal probe having several impedance sensors by normalizing the data, deriving smooth and detail signals for each channel, including localized negative and positive maxima as indications of bolus entry and exit points in the waveform, and then using such information with additional analysis to enhance sensitivity of episode detection, which may include: (i) minimum impedance reached after the episode in distal channels compared to gastric content impedance threshold; (ii) impedance change in distal channels; (iii) variances in the impedance of the distal channels; and (iv) strength of the change in impedance in the swallow direction compared to the impedance change in the reflux direction.

DETAILED DESCRIPTION OF THE INVENTION

Figure 1:
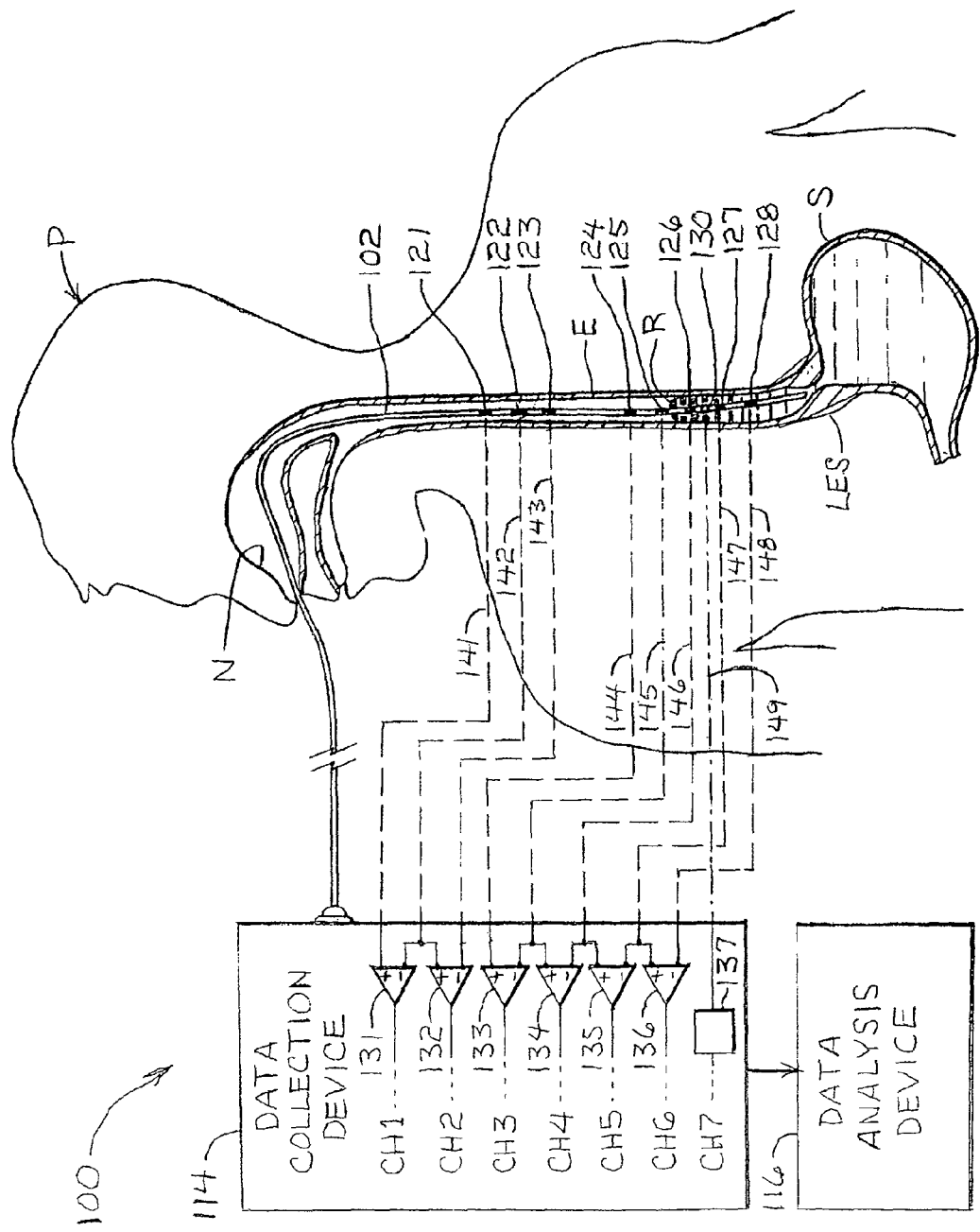
FIG. 1 is a schematic diagram of typical catheter and data recorder equipment used to collect impedance and pH data from a patient's esophagus, and illustrating how a data analysis device using the analysis method of this invention receives data.

A reflux data collection system 100 for collecting impedance data, that may be used in detecting esophageal reflux episodes in a patient P or other test subject according to this invention is illustrated diagrammatically in FIG. 1. Generally, the system 100, which is not part of this invention, includes a long, slender catheter or probe 102 positioned in the esophagus E of a patient or other test subject P with a plurality of impedance electrodes, e.g., electrodes 121, 122, 123, 124, 125, 126, 127, 128, dispersed in spaced-apart relation to each other along the length of the catheter 102 and connected to a data collection device 114. In general, the upper portion of the catheter 102 is referred to as the proximal portion, and the lower portion of the catheter 102 is referred to as the distal portion. Therefore, the upper electrodes 121, 122, 123 are generally called the proximal electrodes, and the lower electrodes 124, 125, 126, 127 and 128 are generally called the distal electrodes. The lowest electrode 128 is the distal electrode. Likewise, the upper channels CH1 and CH2 are generally called the proximal channels, and the lower channels CH3, CH4, CH5 and CH6 are generally called the distal channels. The middle channels CH3 and CH4 may be categorized as distal, proximal, or mid-channels, depending on spacing or the purpose of which the data from such channels are used.

The electrodes 121, 122, 123, 124, 125, 126, 127, 128 are connected electrically to electric circuits or components, e.g., circuits 131, 132, 133, 134, 135, 136, which detect and measure or quantify impedance (opposition to flow of electric current) between adjacent ones of the electrodes 121, 122, 123, 124, 125, 126, 127, 128. The impedance between the electrodes 121, 122, 123, 124, 125, 126, 127, 128 varies depending on what kinds of materials, if any, are touching and bridging the spaces between such electrodes. For example, a liquid reflux (up-flow) R of stomach S contents into the esophagus E, as illustrated in FIG. 1, which are typically liquid and acidic with fairly high ion content, thus good electrical conductors will cause the impedance between the lower electrodes 126, 127, 128, which are immersed in the reflux R, to decrease, as compared to the impedance between those same lower electrodes 126, 127, 128 in the absence of such reflux R and as compared with the impedance between any higher electrodes, e.g., electrodes 121, 122, 123, 124, 125, that may be above the liquid reflux R. Any such change or variation in impedance between any of the electrodes 121, 122, 123, 124, 125, 126, 127, 128 can be detected and measured, thus may be used as an indicator of the presence or absence of reflux R at any of the electrodes 121, 122, 123, 124, 125, 126, 127, 128 at any instant in time. Of course, other materials, such as swallowed liquids and solids in the esophagus E, as illustrated for example by the bolus B in FIG. 2, can also cause changes or variations in impedance as can coughs, hiccups, burps, or even just physical movement. Therefore, a feature of this invention is to detect entry and exit points of a reflux or other bolus on a waveform, i.e., when a reflux or other bolus moves into contact with certain ones of the electrodes and when it clears those electrodes, can be determined, and such information is used in the esophageal waveform analysis described herein. Tracking such entry and exit points, i.e., movement of a reflux or other bolus, across waveforms from multiple channels is useful in determining how they move upward and/or downward through the esophagus.

As mentioned above, impedance can be measured between any of the electrodes 121, 122, 123, 124, 125, 126, 127, 128, and this invention can be adapted in various embodiments to, and used with, any such impedance measurements. However, a typical example arrangement is illustrated in FIG. 1, in which impedance measurements are made between adjacent pairs of closely spaced electrodes on the probe 102, e.g., between electrode pair 121-122, between electrode 122-123, between electrode pair 124-125, between electrode pair 125-126, between electrode 126-127, and between electrode pair 127-128. Thus, each of these six example electrode pairs 121-122, 122-123, 124-125, 125-126, 126-127, 127-128 can be considered as a separate channel CH1, CH2, CH3, CH4, CH5, CH6, for which impedance can be detected, measured and quantified by respective example electric circuits or components 131, 132, 133, 134, 135, 136, as explained above. Of course other electrode configurations, spacings, and pairings can also be used with this invention. Impedance measuring circuits and components are well-known to persons skilled in the art, as are analog and digitizing circuits and components useable for converting the impedance measurements on the six channels CH1, CH2, CH3, CH4, CH5, CH6 from the respective circuits 131, 132, 133, 134, 135, 136 into data that can be logged into and recorded by data collection device 114 on a real time basis and delivered either simultaneously or later to a data analysis device 116. The electrical connections connect the electrodes 121, 122, 123, 124, 125, 126, 127, 128 to the impedance measuring circuits or components 131, 132, 133, 134, 135, 136 in the data collection device 114 are shown schematically in FIG. 1 by phantom lines 141, 142, 143, 144, 145, 146, 147, 148, but, in actual use, they are provided by electric wires (not shown) running through the probe 102, which typically is extended from the data collection device through the patient's nasal cavity N and esophagus E toward or into the stomach S. Of course, alternatives to hard wire connections, such as wireless radio, infrared, or other communications of data from the probe 102 to the data collection device 114 or to the data analysis device 116 can also be used.

While not essential to this invention, it is often helpful to also provide at least one pH sensor 130 in the probe 102 in order to help distinguish between acid and non-acid refluxes R. In the example of FIG. 1, the pH sensor 130 is positioned in the probe 102 between two electrodes 126, 127. Persons skilled in the art know how to position the probe 102 in the patient's P esophagus E so that the pH sensor 130 and electrodes 121, 122, 123, 124, 125, 126, 127, 128 are located at desired spatial relationships to the lower esophageal sphincter (LES) for a particular reflux analysis. The pH sensor 130 is connected electrically to a pH sensor circuit 137 in the data collection device 114, as illustrated schematically by phantom line 149, to provide a seventh data channel CH7 with pH data. Such pH data is also logged into and recorded by the data collection device 114 on a real time basis and sent simultaneously or later to the data analysis device 116. pH sensors, which usually comprise an antimony billet and a reference, are well-known in the art and do not have to be described here for an understanding of this invention.

The probe 102 illustrated in FIG. 1 with its upper or proximal group of electrodes 121, 122, 123 and its lower or distal group of electrodes 124, 125, 126, 127 and a pH sensor 130 positioned between two electrodes 126, 127 in the lower group is merely one of innumerable possible configurations that can be used with this invention to detect and quantify esophageal reflux episodes. As can be seen from the illustration in FIGS. 1 and 2 and the description above, and as will be explained in more detail below, a liquid reflux R moving from the stomach S, through the LES, and into the esophagus E will cause a drop in impedance, first in the distal channel 6 (CH6), then in channel 5 (CH5), and continuing in sequence to CH4, CH3, CH2, and CH1, depending on how far the liquid reflux R moves upwardly into the esophagus E, thus on how many of the electrodes 121-138 it reaches. For example, if the reflux R in FIG. 1 moves upwardly from the stomach S and through the esophagus E far enough to reach the electrode 125 and then recedes back into the stomach S, idealized waveforms of impedance (A) on a time scale (T) for the channels CH1-CH6 would appear something like the idealized waveforms 231, 232, 233, 234, 235, 236, 237 in FIG. 3. Specifically, as the reflux R moves upwardly in the esophagus E, it gets high enough first to bridge the lowest electrode pair 127-128, so the impedance between those electrodes 127, 128, as measured on channel CH6, drops to a lower level 236' at approximately time $t_1$. As the reflux R continues to move upwardly, it next bridges the electrode pair 126-127, so that the impedance between those electrodes 126, 127, as measured on channel CH5, drops to a lower level 235' at approximately time $t_2$. Likewise, as the reflux R continues to move upwardly in the esophagus, it next bridges the electrode pair 125-126, causing a drop in impedance on channel CH4 to a lower level 234' at about time $t_3$, and then continues upwardly to bridge electrode pair 124-125 to cause a drop in impedance on channel CH3 to a lower level 233' at about time $t_4$. Since, in this example, the reflux R does not reach the upper electrodes 121, 122, 123, the impedance waveforms 221, 222 on channels CH1 and CH2 do not change. If the reflux R did reach the upper (proximal) electrodes 121, 122, 123, which would not be unusual, the resulting changes in impedance on CH2 and CH1 would, of course, also be seen in the waveforms 332, 331 for those channels.

Then, as the liquid reflux R recedes and flows back down the esophagus E and into the stomach S, thus clearing the electrodes one by one on is way back toward the stomach S, the impedance measured on those of the channels that dropped due to the liquid reflux R will increase again back toward normal (base) levels.

In the example described above and shown in FIG. 3, the receding liquid reflux first clears the electrodes 124, 125 at about time $t_5$, so the impedance on channel CH3 rises again to its base, i.e., normal, level 233". Likewise, as the liquid reflux R continues receding toward the stomach S, it clears the electrodes 126, 127, 128 in sequential order at about times $t_6$, $t_7$, $t_8$, respectively, thereby causing corresponding sequential returns of impedance on channels CH4, CH5, CH6 to their base, i.e., normal, levels 234", 235", 236", respectively.

Figure 3:
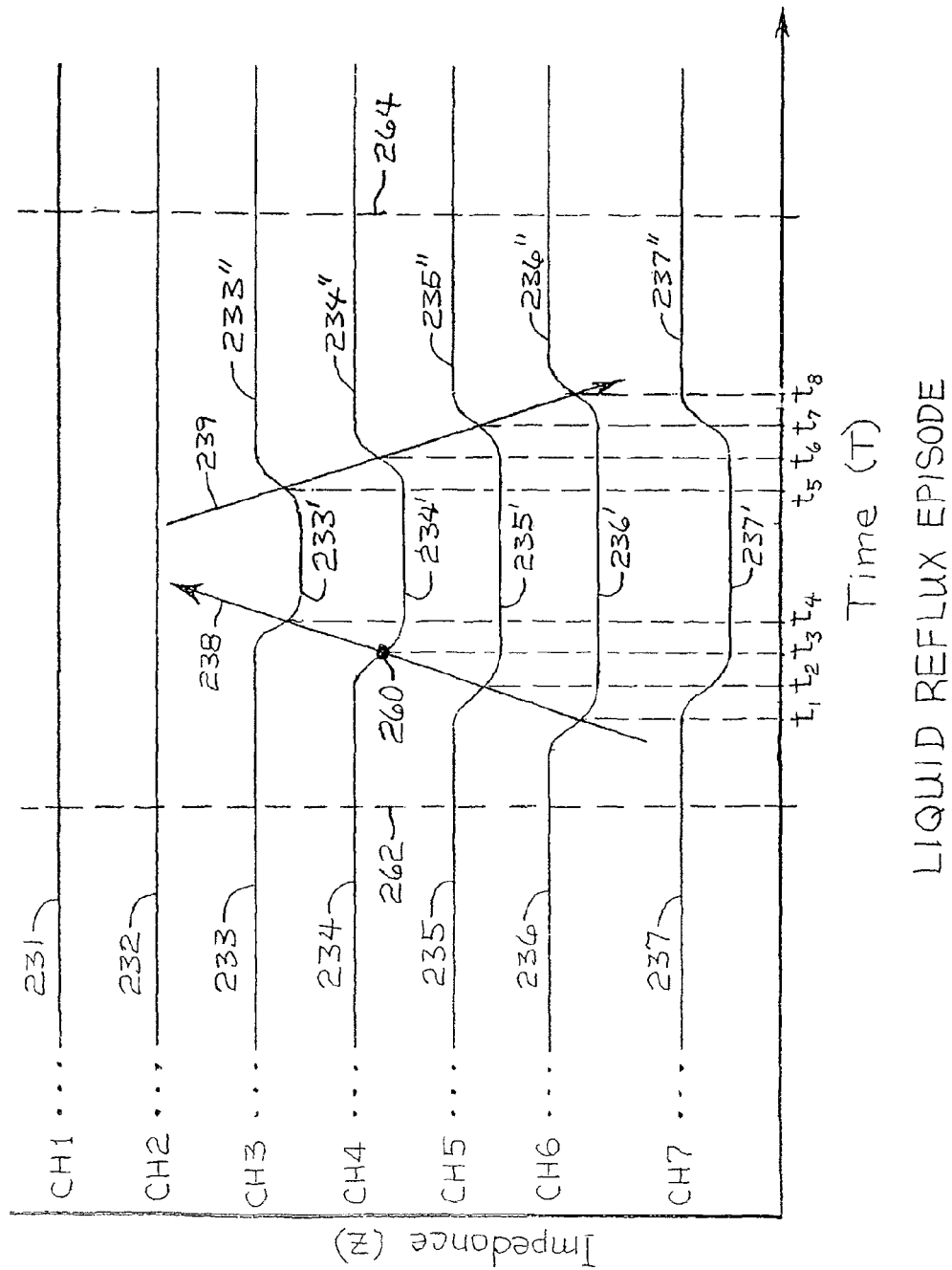
FIG. 3 is a graph showing idealized multiple impedance channel waveforms and an idealized pH channel waveform as an idealized example illustration of a typical liquid reflux episode.

It should be noted that the example impedance curves for the example channels CH1 through CH6 and the example pH curve for the example pH channel CH7 in FIG. 3 is very idealized to illustrate the principles being described. In reality these curves are not smooth, and, due to noise and many other factors, such reflux episodes are not nearly as easy to see and find. Therefore, wavelet transform analysis and other test criteria are used to detect reflux episodes from impedance signals and, optionally, from impedance and pH signals, as will described below. Also, gas reflux would be manifested as almost instantaneous, sharp rise in impedance instead of the classic drop in impedance shown by the impedance curves in FIG. 3, as will be explained below. Therefore, an analysis of data waveforms of the channels CH1-CH6 that shows, for example, a drop of impedance first in CH6, then in channel CH5, then in CH4, and sequentially on through additional channels, followed by sequential rises of impedance in reverse sequential order, would indicate that a liquid reflux R episode has occurred, i.e., that liquid material from the stomach S has escaped the stomach S through the LES for some reason and has moved upwardly in the esophagus E and then returned to the stomach S over some time period. In the example described above and illustrated in FIG. 3, such sequential drops in impedance on channels CH6, CH5, CH4, CH3, i.e., starting with the distal electrode pairs 127-128 closest to the stomach S and moving upwardly, and then returning to their base levels 233", 234", 235", 236" in reverse sequential order, is indicative of a liquid reflux episode that occurred during a time period extending from the time $t_1$, to time $t_8$. Such upward movement of the liquid reflux R in FIG. 3 is plotted through the waveform transitions on channels CH6, CH5, CH4, CH3 from base level to lower level impedances at the times $t_1$, $t_2$, $t_3$, $t_4$ by the arrow 238, which has a positive, upward slope, i.e., upward with advancing time. Similarly, the subsequent downward movement of the liquid reflux R back toward the stomach S is plotted through the same channels in their transitions back to base level at times $t_5$, $t_6$, $t_7$, $t_8$ by the arrow 239, which has a negative slope, i.e., downward with advancing time. These arrows 238, 239 illustrate graphically the upward surge of liquid refluxate R from the stomach S into the esophagus E and its recession back into the stomach S.

As mentioned above, it can be helpful to also have one or more pH sensors on the probe 102 for sensing the pH level. In the example configuration shown in FIGS. 1 and 2, there is one pH sensor 130 positioned between electrodes 126, 127, and the pH sensed by the sensor 130 is read, measured, and reported on channel CH7. In the example liquid reflux episode described above and illustrated by FIG. 3, the pH on channel CH7, shown by waveform 237, drops to a lower level 237' at about the same time $t_2$ as the impedance drops on channel CH5, i.e., when the liquid reflux R in FIG. 1 reaches the pH sensor 220, and it rises again to its base—i.e., normal—level 237" at about the same time $t_7$ as the impedance on channel CH5 returns to its base level 235". Such drop in pH on channel CH7 indicates the reflux R is acidic, as opposed to a non-acidic reflux.

A non-acidic reflux is also possible, but not shown in FIG. 3. For example, if the patient P is taking medicine to control acid in the stomach S, a liquid reflux R might not be acidic. In that case, the pH curve 237 for CH7 would not drop during the reflux episode.

Figure 2:
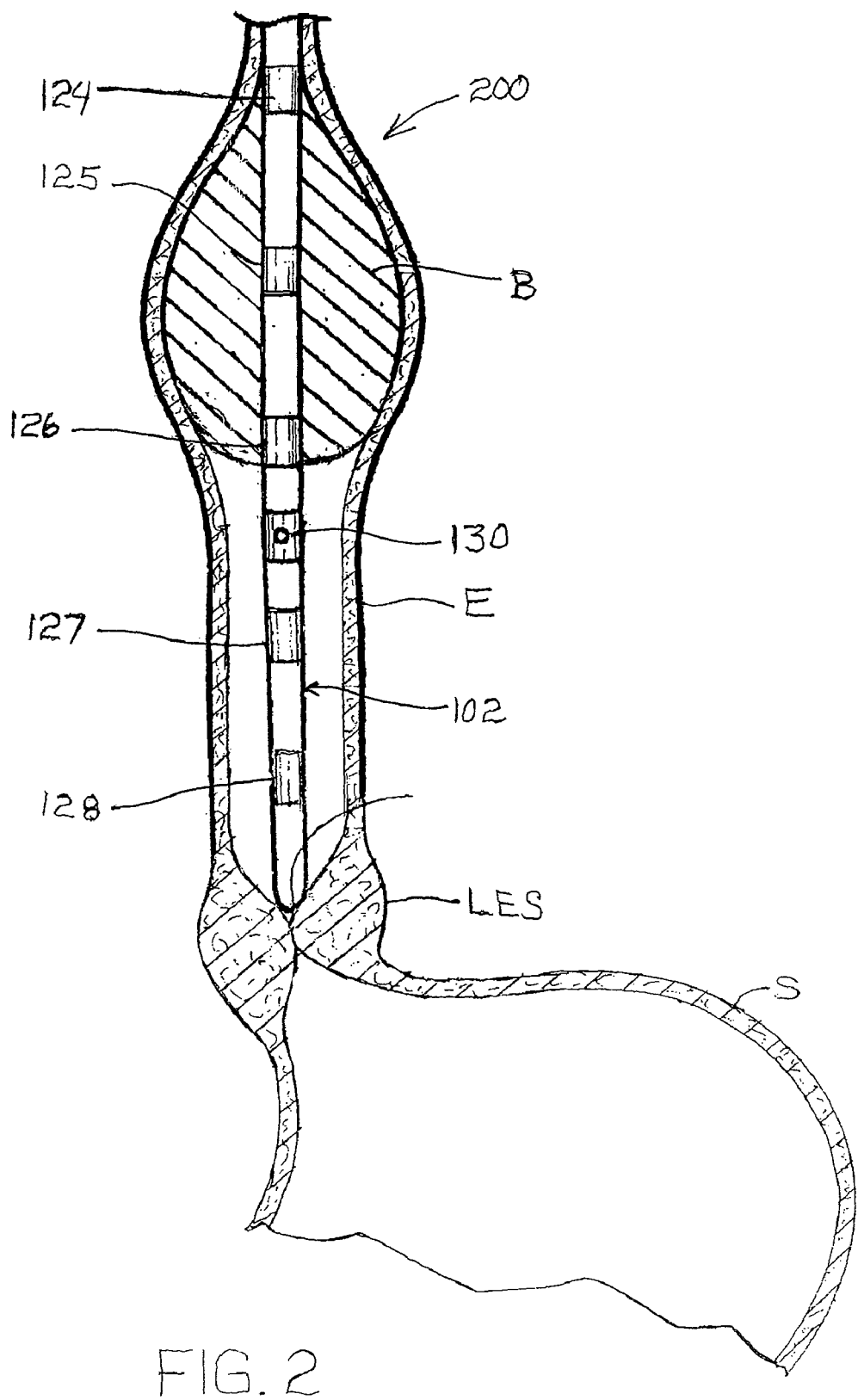
FIG. 2 is a cross-sectional view of a lower portion of a catheter in an esophagus with a bolus to aid in explaining the origination of data that is analyzed by this invention.
Figure 4:
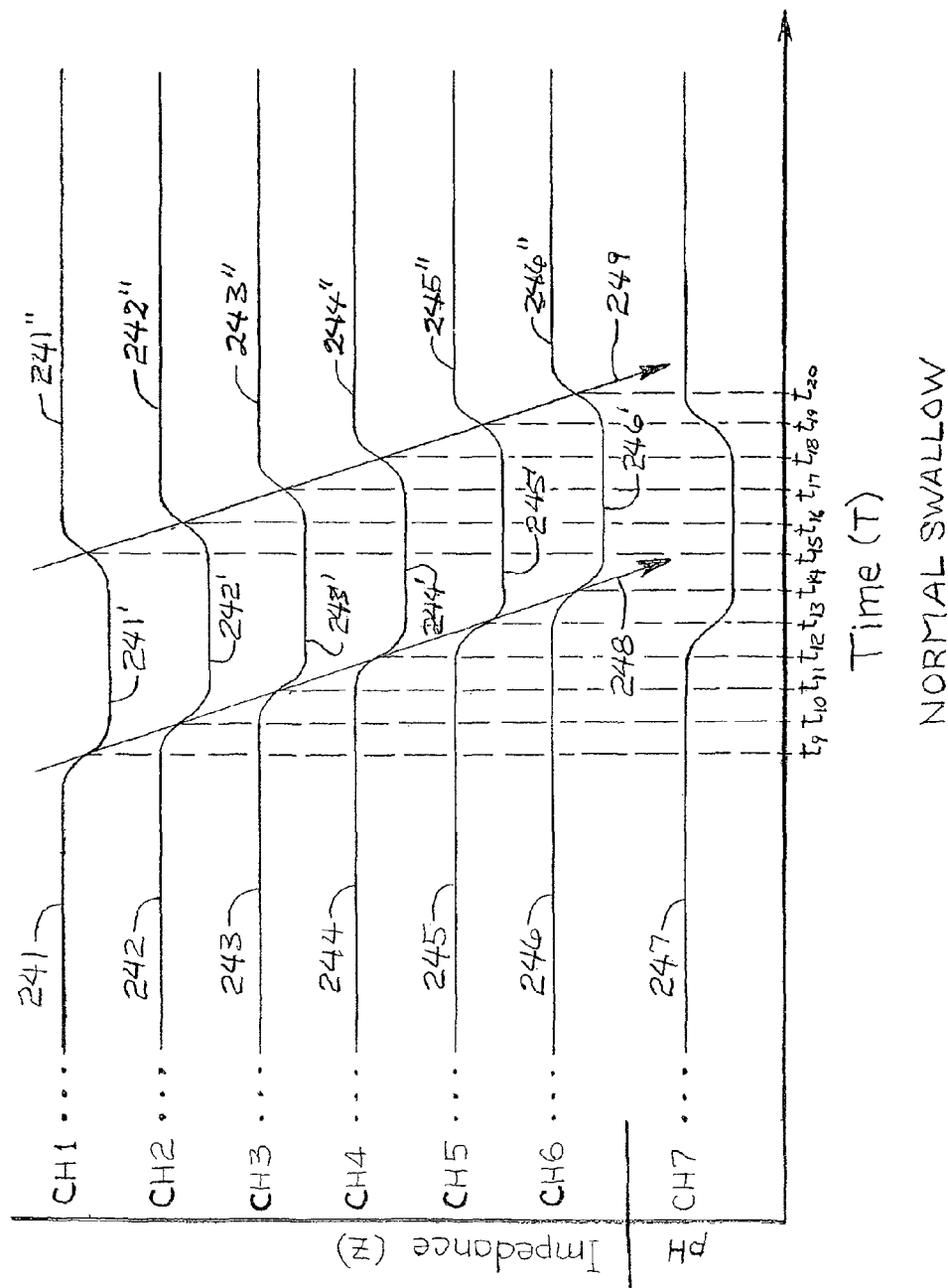
FIG. 4 is a graph showing idealized multiple impedance channel waveforms and an idealized pH channel waveform as an idealized example illustration of a normal swallow.

In contrast to the waveforms of the liquid reflux episode illustrated in FIG. 3, a swallow of low impedance material, which moves from the mouth of the patient P down through the esophagus E to the stomach S, as depicted by the bolus B in FIG. 2, results in a different series of waveforms, as illustrated in FIG. 4. The bolus B of swallowed material will also cause drops in impedance, first in the upper or proximal channel CH1 and then sequentially down through subsequent channels CH2, CH3, CH4, CH5, CH6, as the bolus B of swallowed material moves downwardly and contacts the electrode pairs 121-122, 122-123, 124-125, 125-126, 126-127, 127-128 sequentially, followed by rises of impedance in the same sequential order of the channels CH1-CH6 as the bolus B of swallowed material clears the electrodes 121-128. Therefore, an analysis of data waveforms of channels CH1-CH6 in FIG. 4, which shows that kind of impedance pattern, would not be indicative of a reflux episode. Again, the impedance and pH curves in FIG. 4 are very idealized and would not be nearly as easy to read in real curves from real patient data.

For example, a normal swallow comprising a bolus B of food or other material, as shown in FIG. 2, beginning at the mouth (FIG. 1) and moving downwardly in the esophagus, first encounters and bridges the first electrode pair 121-122 (shown in FIG. 1, but not seen in the enlarged view of FIG. 2), so the impedance between those two electrodes 121, 122 as measured on channel CH1 drops. Therefore, the impedance waveform 241 for channel CH1 illustrated in FIG. 4 also is the first to drop at a time $t_9$ to a lower level 241'; and then it rises back at a time $t_{15}$ to base level 241" as the bolus B continues down the esophagus E and clears the area between the two electrodes 121, 122. Likewise, as the bolus B of food continues moving downwardly through the esophagus E and sequentially encounters and bridges the remaining electrode pairs 122-123, 124-125, 125-126, 126-127, 127-128, the respective impedance waveforms 242, 243, 244, 245, 246 on channels CH2, CH3, CH4, CH5, CH6 drop at respective times $t_{10}$, $t_{11}$, $t_{12}$, $t_{13}$, $t_{14}$ to lower levels 242', 243', 244', 245', 246', before the return to their respective base impedance levels 242", 243", 244", 245", 246". The negative downward slopes (i.e., downward with advancing time) of both of the arrows 248, 249 of the sequential transitions downwardly and upwardly in FIG. 4 indicate a bolus traveling only downwardly from the pharynx or upper esophagus (depending on electrode placement), to the stomach S, i.e., a normal swallow.

Figure 5:
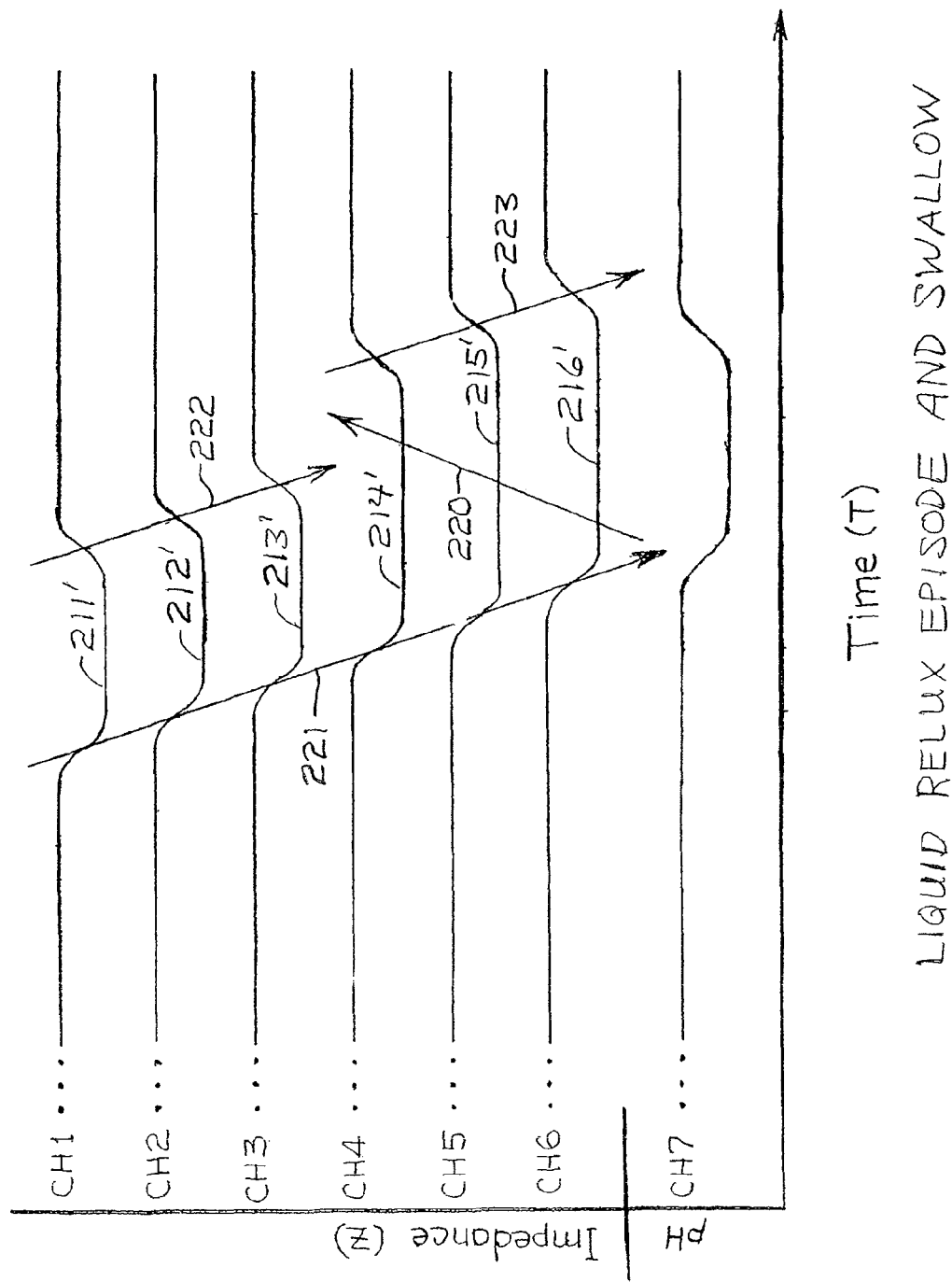
FIG. 5 is a graph showing idealized multiple impedance channel waveforms and an idealized pH channel waveform as an idealized example illustration of a liquid reflux episode occurring along with a swallow.

The episode illustrated by the waveforms in FIG. 5 is an example of a liquid reflux indicated by arrow 220 following a swallow indicated by arrows 221, 222. The arrow 223 shows the liquid reflux clearing, but on a delayed time line as compared to the swallow arrow 222. Essentially, the reflux 220 in this example begins as the swallow bolus B (not shown in FIG. 5, but shown in FIG. 2) reaches the LES, and it reaches a height of about a mid-channel, e.g., channel CH4, before clearing. This kind of liquid reflux partially obscured by a swallow is more difficult to detect than the liquid reflux in FIG. 3, but a characteristic includes longer periods of low impedance 214', 215', 216' in the more distal channels CH4, CH5, CH6 than the periods of low impedance 211', 212', 213' in the more proximal channels CH1, CH2, CH3.

Figure 6:
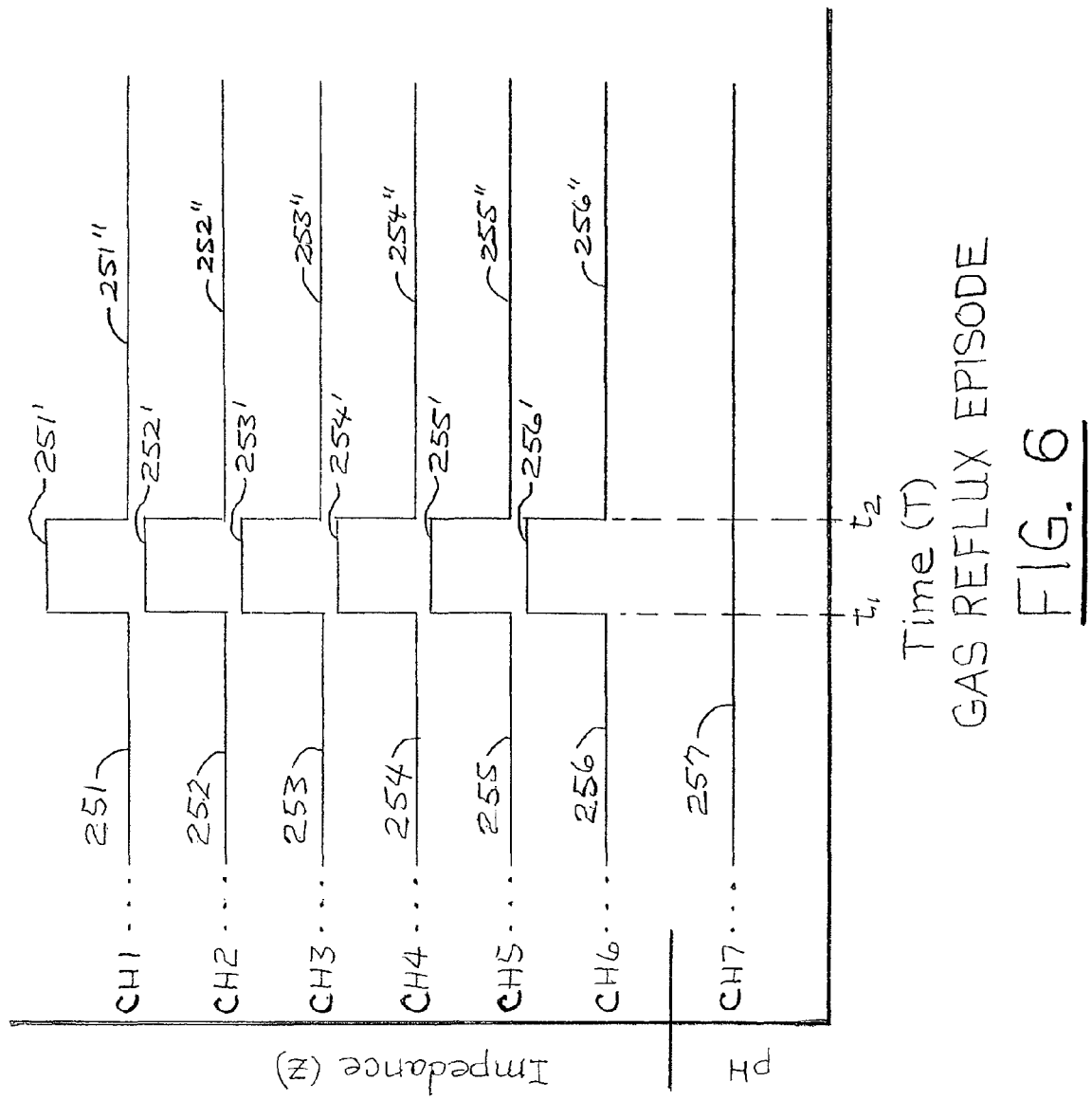
FIG. 6 is a graph showing idealized multiple impedance channel waveforms and an idealized pH channel waveform as an idealized example illustration of a gas reflux episode.

A gas reflux, unlike a liquid reflux, causes a sharp, almost instantaneous rise of impedance across any electrode pair that it reaches in the esophagus E, because gas is generally not conductive of electricity and because it travels very fast through the esophagus E. Therefore, a gas reflux episode may cause the almost instantaneous sharp rise of impedance from base level 251, 252, 253, 254, 255, 256 on one or more channels CH1, CH2, CH3, CH4, CH5, CH6 to a substantially higher level 251', 252', 253', 254', 255', 256', as illustrated in FIG. 6. The gas could clear almost as quickly causing an almost instantaneous decrease in impedance back to base level, as indicated at 251", 252", 253", 254", 255", 256", or it could linger for long periods of time at any or all of the electrode locations (not shown in FIG. 6). The pH on CH7, wave curve 257, may or may not change during a gas reflux episode.

In reality there are also combinations of liquid and gas reflux, swallows occurring at the same times as refluxes, coughs, and other causes, which may be difficult to determine. However, reflux patterns can generally be categorized as either liquid reflux, mixed reflux, or gas reflux, as follows:

Liquid Reflux:

Impedance changes from patient impedance (baseline) to a low value in at least two channels and the inverse pulse shape propagates upwardly. The important factor is the impedance change and not the minimum impedance reached during the episode. The minimum impedance reached depends on many factors including stomach contents and refluxate position with respect to the channel.

Inverse pulse shape propagates from the distal channel to the next higher channel, and so on.

Most of the time, clearance of reflux occurs in the higher channel before the lower, and the last channel to be cleared is the distal channel. This pattern corresponds to a continuous reflux.

pH alone is not enough to determine reflux. Reflux could occur with or without pH change, and pH drop may or may not be as a result of reflux.

Mixed Reflux:

Impedance changes from patient impedance (baseline) to a low value in at least two channels, and the inverse pulse shape propagates upwardly. An impedance change to a very high value in at least two channels occurs any time during the episode duration. Most of the time, the change occurs either in the two distal channels or in the two proximal channels and at the start of the episode.

Inverse pulse shape propagates from the distal channel to the higher channel, and so on.

pH alone is not enough to determine reflux. Reflux could occur with or without pH change, and pH drop may or may not be as a result of reflux.

Gas Reflux:

Gas reflux can be identified by sharp narrow instantaneous change in impedance to a high value in at least two channels. Most of the time, this change occurs either in the most distal or the most proximal channels. It also could be a sharp, narrow, instantaneous change in impedance to a high value in the distal channel accompanied by a pH drop.

A problem, however, is that such impedance data waveforms in actual conditions do not always conform so clearly to such ideals. For example, a reflux episode can occur at the same time as a swallow, which makes a more complex waveform and complicates the analysis. Also, a reflux R can pool above the LES and not return immediately to the stomach S, which also complicates detection of reflux R episodes. Further, baseline impedances can vary from person to person or even in an individual over time. These and other complications, compounded by electronic noise and myriad [[of]] physical causes of variations in the impedance measurements, make it very difficult to detect reflux episodes in the waveforms. A feature of this invention is to automate classification of reflux episodes detected in such waveforms. In general, wavelet transforms are applied to the signals from all the channels to identify significant impedance changes in the waveforms, which are then analyzed to determine the propagation of such impedance changes by tracking the shapes of the impedance waveforms. Decision-making then involves one or more of the following rules: (i) Rules for normal signals; (ii) Rules for low baseline signals, e.g., for patients who have lower impedance baseline levels than normal; and (iii) Rules for acid reflux episodes.

The data collection device 114 may receive and store the data from the various sensors, e.g., electrodes 121-128, pH sensor 220, and the like, on the probe or catheter 102 on an ongoing basis. In a typical 'long term' study, a patient may have the catheter 102 in place for 24 hours or more. In such a case, the data collection device 114 may be a portable data collection device that is worn by the patient P in a pouch (not shown), clipped onto a belt (not shown), or worn or carried in any other manner. In a 'short term' study, or one where the patient P is not ambulatory, the data collection device 114 may be a stand alone computer or otherwise not be portable.

The data analysis device 116, which includes hardware and software for performing the wavelet analysis to identify possible events, can be used to analyze the data collected on the several channels CH1-CH7 from the catheter 102. The data collection device 114 and the data analysis device 116 may be the same piece of hardware but, usually the data collection device 114 and the data analysis device 116 are separate, such as when the data collection device 114 is a portable device clipped on the patient's belt and the data analysis device 116 may be a computer with a display and keyboard located in a health care professional's office or laboratory.

Figure 7:
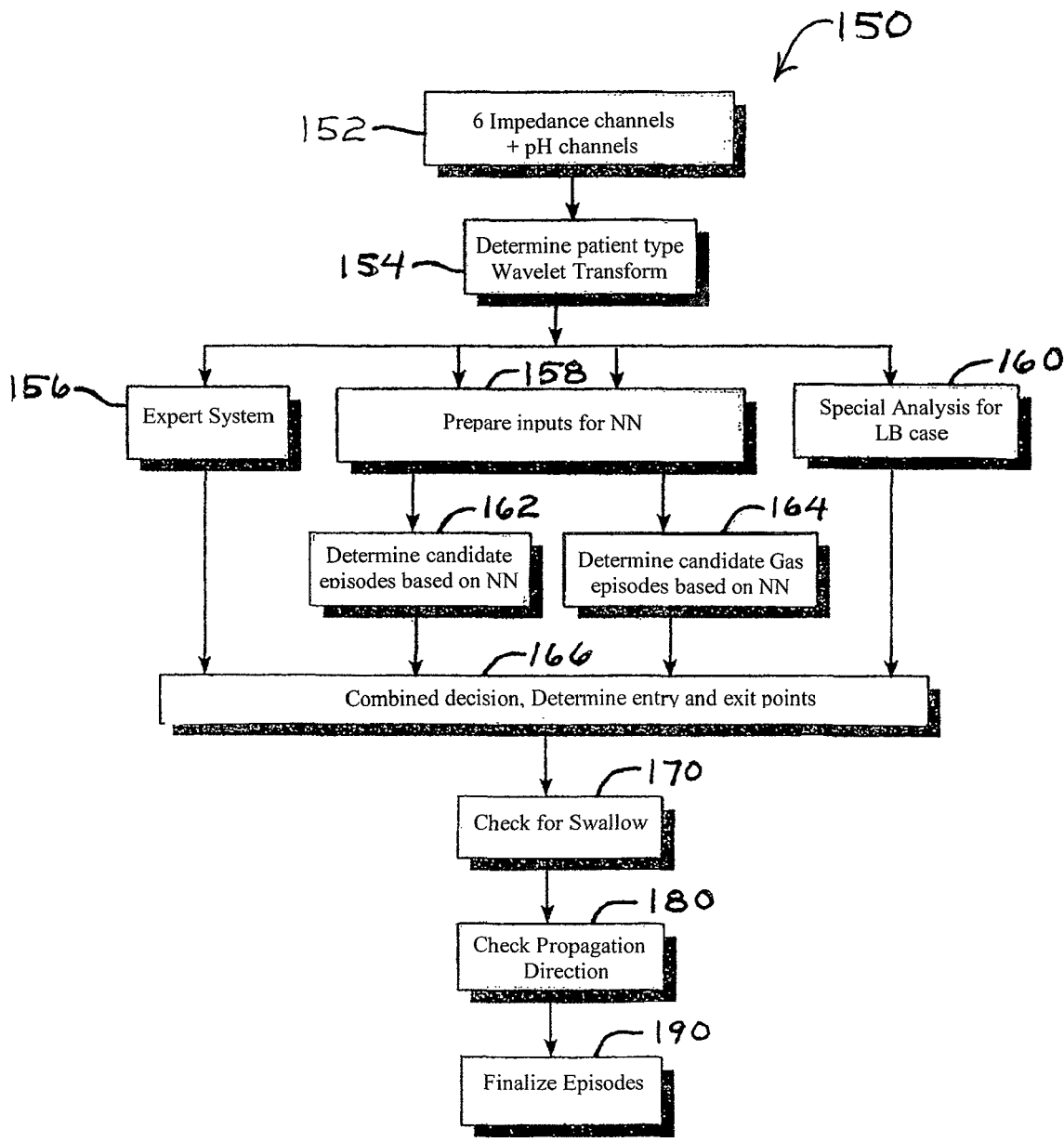
FIG. 7 is a function block diagram illustrating a process for detecting and characterizing gastrointestinal episodes in which this invention is used.

The main stages of a system 150 for detecting and classifying reflux episodes from intraluminal impedance data and classify them according to their contents, such as liquid, mixed liquid and gas, or gas, is shown in FIG. 7, parts of which include the analysis method of this invention. While any number of impedance channels and pH channels can be used, this example system continues with the example of six impedance channels and one pH channel as described above. The stages can be reiterated any number of times with some components added or omitted as desired.

The data is collected from the impedance channels and pH channel at 152 and is fed to the function 154, which applies wavelet transform and analysis, to find possible episodes in the data. The function 156, sometimes called the Expert System, uses statistics and Boolean logic to identify episodes when the patient has normal baseline impedance levels and to determine the patient type, i.e., whether the patient has normal high baseline impedance levels in his or her esophagus or abnormal low baseline impedance levels. As mentioned above, abnormal low baseline impedance levels can result from a history of repeated acid reflux episodes or esophagitis, which often causes erosion and ulceration of esophageal mucosa, which, makes mucosa membrane conductivity change in relation to healthy tissue. The analysis of data from patients who have low baseline impedance is more challenging, since there is a smaller dynamic range for signal variations. Therefore, low baseline data is detected at function 154 and identified for special analysis 160 adapted for that kind of data, as will be explained below. Essentially, whenever the waveform analysis shows that the value of the patient impedance as well as change in impedance during gastrointestinal events are low, then such waveforms are treated as low baseline waveforms.

The wavelet transform at function 154 includes applying a smoothing algorithm to eliminate meaningless noise and to provide more meaningful and manageable waveforms, and to sum energy in the negative details and in the positive details useable for determining significant transitions in the waveforms and times of such transitions.

The results of the wavelet transform are analyzed in a number of ways. The function 156, called "Expert system" performs analyses on the wavelet transform results from all the channels to determine possible classifications of events from impedance transitions, times of transitions, magnitudes of transitions, propagation directions, limits of propagation, and the like for possible liquid reflux episodes, mixed liquid and gas reflux episodes, gas reflux episodes, and whether the episodes are acid or non-acid.

The wavelet transform analyses of esophageal impedance waveforms are sensitive and can identify possible episodes very effectively, by locating possible bolus entry and exit points, if any, in each impedance waveform and by locating retrograde movement episodes across impedance channel waveforms and some additional processing. Once the results of this wavelet transform analysis according to this invention are obtained so that possible reflux episodes are identified in the data, persons skilled in the art can review them and further characterize them for valid liquid reflux or other episodes or eliminate them as invalid, i.e., false positives, based on experience in recognizing distinguishing characteristics, combinations of characteristics, overall appearances, etc. While not required by this invention, it is possible to automate a system to replicate these kinds of further reviews to eliminate at least some of the false positives that might be included in the waveform analysis results of this invention, and there are a number of methods that could be used for doing so. Neural networks have been used to help in the detection of reflux waveforms identified by other systems. Candidate waveforms identifiable by the analysis of this invention can increase the effectiveness of neural networks used to make comparisons with normalized waveforms selected by experts in the field as being representative of certain kinds of episodes to reduce false positives, i.e., to eliminate possible episodes that are not as likely to be actual episodes. There are many kinds and forms of neural networks that can be used for this purpose as would be understood by persons skilled in the art, once they understand the principles of this invention. For example, the function of neural network 162 in FIG. 7 is to process reflux episodes identified by the waveform analysis process of this invention that have large impedance changes, i.e., for patients that do not have low baseline impedances, to see if they are close enough to examples of normalized waveforms selected by experts in the field to be counted as certain kinds of liquid refluxes. These episodes reviewed by neural network 162 can include liquid reflux, mixed liquid and gas reflux, and gas reflux. However, since it is often easier to identify gas separate from liquid reflux and mixed liquid and gas reflux episodes, a second neural network 164 may be included to find only gas reflux episodes.

In addition to the inputs from the neural networks 162, 164, further analysis can take input from the wavelet analysis function 156 and from the special low baseline analysis function 160. Such analysis can combine these inputs to assimilate the statistics obtained from all the stages, to further refine the classification of episodes, and to thereby make decisions as to whether the possible gastrointestinal events identified by the wavelet analysis of this invention fit within patterns that are understood by experts in the field to be indicative of actual liquid reflux events, e.g., liquid/acid reflux, liquid/non-acid reflux, gas and liquid contents (mixed)/acid reflux, and mixed/non-acid reflux.

Two additional checks are made in the example process 150 of FIG. 7. In function 170, the data is checked to be sure the episode is not a result of a pre-episode swallow, as will be described below, and the function 180 checks to make sure that the propagation direction of the inverse impedance pulse is from the distal to the proximal. Failure of the episode to pass either of these checks at 170, 180 indicates that the event is not a reflux episode.

The final classifications of events from the data as reflux episodes can be reported out at function 190 for any desired use, such as tallying total reflux episodes over the data gathering period, frequencies of reflux episodes, kinds of reflux episodes, ratios, and the like.

In reference now to function 154 in FIG. 7 and to FIGS. 3-6, researchers and clinicians have determined that certain features and characteristics in the impedance waveforms can be indicative of reflux episodes and other esophageal events of interest. The problem, first, is to find such features, which may comprise only a few seconds or less in twenty-four hours or more of data. A preferred method of finding such features is to locate transition points in the waveform that may indicate at least a point in a feature of the waveform that might be of interest, e.g., that might be indicative of a reflux episode. Referring to FIG. 3, which, for simplicity, shows only idealized waveforms, an example transition point on the waveform of CH4 may be the transition point 260, where a declining impedance transitions toward leveling out, also referred to as a singularity in the waveform. It is a point where the rate of change in the slope of the curve is zero. It can be seen in this context that transition point 260 is, indeed, a point on a waveform, which, together with the waveforms of other channels CH3, Ch5, CH6, could be indicative of a liquid reflux episode. However, a computer, upon finding this singularity or transition point 260, would not yet have the benefit of the other waveforms or even the rest of the significant features in that same waveform, to know that it is at or near the start of a liquid reflux episode. Therefore, the point 260 and its time of occurrence ($t_3$ in FIG. 3) is recorded, and the system can mark a section of that waveform between a start point or time 262 and an end point or time 264 for further analysis. The start point 262 can be some arbitrary time, such as a several seconds, before the time $t_3$ of the identified transition point or singularity 260, and the end point 264 can be some arbitrary time after the time $t_3$ of the transition point 260, preferably enough to capture the portion of the waveform that shows the entire event.

The first task in this operation, therefore, is to identify the singularities or transition points in the waveform traces from all of the impedance channels. In reality, as mentioned above, impedance traces, i.e., data read-outs and collection from impedance probes 102 (FIG. 1), are far from any idealized waveforms due to various factors such as noise, changes due to patient movement, respiration, etc. Sharp variations occur due to events in the gastrointestinal tract caused by air that is often in front of the reflux and bolus materials or by the bolus or refluxate material entering or leaving a measurement segment (i.e., the space between the electrode pair from which the data or trace is being read). These variations can be modeled mathematically as singularities. Multiresolution analysis using wavelets is used to address this problem.

If a wavelet is chosen as the first derivative of a smoothing function (any function whose integral is equal to 1 and asymptotically reaches 0), and if the first and the second derivative of the function exists, then the local maxima of the absolute value of the wavelet transform can be used to detect the occurrences of such singularities, i.e., transition points, in the waveform that may indicate the beginning or end of an episode and possibly of a reflux episode.

To obtain a wavelet with symmetry and compact support, wavelet $\psi(t)$ and its dual $\overline{\psi}(t)$ are chosen to be linearly independent and satisfy the bi-orthogonality condition as:

$$<\psi_{m,n}(t), \overline{\psi}_{k,l}(t)> \geq \delta(m-l)\delta(n-l) \qquad (1)$$

Such wavelet functions can be constructed by using a cascade of perfect reconstruction filters. For detection, a wavelet $\psi(t)$ is chosen to be equal to the first derivative of a smoothing function implying that $\psi(t)$ must have a zero of order 1 at $\omega=0$ in the frequency domain. The Fourier transform of a wavelet which satisfies the above properties is:

$$\Psi(\omega) = -\frac{i\omega}{4}\left(\frac{\sin(\omega/4)}{\omega/4}\right)^4 e^{-i\omega/2} \quad (2)$$

$\Psi(\omega)$ corresponds in time domain to a derivative of a function whose Fourier transform is:

$$\Theta(\omega) = \left(\frac{\sin(\omega/4)}{\omega/4}\right)^4 e^{-i\omega/2} \quad (3)$$

which is the delayed fourth order convolution of a rectangular function. A spline wavelet is used in this analysis, although other wavelet forms could be used. These wavelets and scaling functions can be constructed using a cascade of perfect reconstruction filters $(h,\tilde{h})$ and $(g,\tilde{g})$ that satisfy $$H^*(\omega)\tilde{H}(\omega) + H^*(\omega+\pi)\tilde{H}(\omega+\pi) = 2 \quad (4)$$

and $$G(\omega) = e^{-i\omega}\tilde{H}^*(\omega+\pi);\ \tilde{G}(\omega) = e^{-i\omega}H^*(\omega+\pi) \quad (5)$$

Wavelet analysis can be used to develop the smooth version $A_{j+1}(k)$ and detail version $D_{j+1}(k)$ of the waveform, as follows:

$$A_{j+1}(k) = \sum_{n=-\infty}^{\infty} h(n-2k)A_j(n) \quad (6)$$

$$D_{j+1}(k) = \sum_{n=-\infty}^{\infty} g(n-2k)A_j(n) \quad (7)$$

In addition, such decomposition can be accomplished for many resolution levels successfully.

Figure 8:
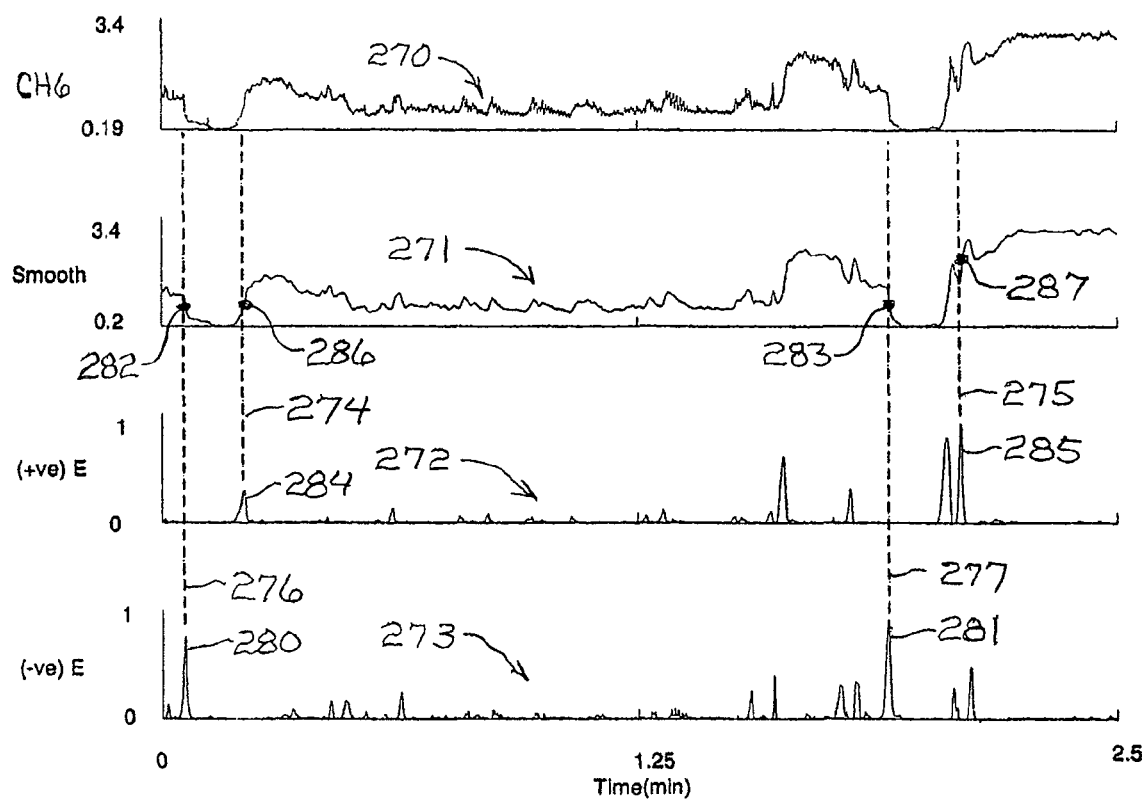
FIG. 8 is a graph showing an example impedance channel waveform processed according to this invention to produce a smooth waveform and detail waveforms of localized positive and negative maxima used to find bolus entry and exist points.

Wavelet transformation may be applied to the waveforms from all the channels, e.g., channels CH1-CH6 in the example described above, resulting in a detail signal and a smooth signal for each channel. FIG. 8 shows an example impedance waveform 270, the resulting smoothed version 271, and the sum of energy in the details from levels (2-5) of the multi-resolution analysis. The details are further classified into positive values 272 and negative values 273. The positive details 272 correspond to the positive slopes in the impedance, and the negative details 273 correspond to the negative slopes. This relationship can be seen by observing that the negative maxima peaks corresponding to broken lines 276, 277 align with the corresponding negative slopes in the smoothed waveform 271. Likewise, it can be observed that the positive maxima peaks corresponding to broken lines 274, 275 align with the corresponding waveform 271. The sum of the energy in the negative details and that of the positive details are also shown. Broken lines 274, 275 show locations of positive detail maxima, and broken lines 276, 277 show locations of negative maxima. The location 276 or 277 of a maxima of negative details corresponds to the occurrence of a candidate episode, especially if it simultaneously appears propagating across channels. Similarly, the location 274 and 275 of a maxima of positive details corresponds to the end of the episode.

Respiration artifacts are rejected by monitoring the location between successive maxima of the sum of the energy in the negative details (i.e., frequency range 0.2 to 0.33 Hz). This operation can be facilitated by performing wavelet transformation in the frequency domain.

As can also be observed in FIG. 8, the negative and positive maxima correspond to transition points in the smoothed waveform 271. Therefore, negative maxima 280, 281 correspond to transition points 282, 283, respectively, as shown by broken lines 276, 277. Likewise, positive maxima 284, 285 correspond to transition points 286, 287, as shown by broken lines 274, 275. As explained above, a candidate transition point requires a defined end point. Therefore, points 282 and 283 illustrate candidate transition points, while points 286 and 287 illustrate candidate end points. The candidate transition points are identified by the local maxima of the negative movements 273. Correspondingly, the end points are identified by local maxima of the positive movements 272.

From a signal description perspective, if the change in impedance in the two distal channels CH5, CH6 is large (i.e., the mean of the distribution of minimum to baseline impedance $\leq 0.51$), then these signals are termed normal. When the mean of the distribution of minimum to baseline impedance $> 0.5$ and $\leq 0.8$, then these signals are termed semi-normal. The series of the times at which the impedance exhibit transition to the gastric content at each channel starting from the most distal channel is referred to as the propagation direction, as illustrated by arrow 238 in FIG. 3. Initial propagation direction is determined from the energy of the wavelets coefficients of the three distal channels, CH6, CH5, CH4, and then the mid-channel CH3 and proximal channels CH2, CH1 are added. The impedance of gastric contents $(Z_c)$ along with the propagation direction are sufficient information to determine a well defined episode. But in reality, all episodes may not be "well defined". Some examples are:

a) Refluxes after swallow will result in propagation impedance waveform shapes that will meet at a mid-channel, e.g., CH3.

b) Patient impedance $(Z_p)$ is close to gastric contents impedance $(Z_c)$, and c) Undetermined propagation direction due to closely spaced episodes.

Additional analysis is performed to enhance the sensitivity of episode detection. The following additional parameters are evaluated to assist in the analysis:

i. Minimum impedance reached after the episode in CH6 and CH5 compared to gastric content impedance threshold (to help distinguish true exit from gas bubble interference);

ii. Impedance change in CH6 and CH5 (large changes yield greater confidence in episode detection);

iii. Variances in the impedance of the distal three channels CH6, CH5, CH4 (low variances give greater confidence in episode detection); and iv. Strength of the change in impedance in the swallow direction compared to the impedance change in the reflux direction (a large impedance change indicates "heavy" material which could cause a "bounce back" splash simulating a reflux).

All of the above parameters are used in a combined decision-making process, with emphasis on the gastric contents threshold and the propagation direction.

Reflux could be acidic or non-acidic depending on pH value a few seconds after the episode. Therefore, two gastric contents impedance thresholds are used—one corresponding to acid reflux episodes and one corresponding to non-acid reflux episodes. Where there is pH support for impedance indications of acid episodes, acid episodes are easier to define, so a more general threshold can be used. Non-acid episodes, where there is no pH support, are more difficult to spot, so a more granular threshold is used. To determine these thresholds, one pass over a longer stretch of data, such as about 2.27 hours of data, may be used to determine an initial gastric content impedance by performing clustering analysis of the impedance value during the episodes. More information about cluster analysis can be found in the following articles: S. Chiu, "Fuzzy model identification based on cluster estimation," J. Intell. FUZZY Syst. (1994); and. Al-Zaben et al., "Detection of Gastrointestinal Tract Events from Multi-channel Intraluminal Impedance Measurements", Biomedical Sciences Instrumentation, Vol. 37 (2001). Essentially, it strives to find a "smart" average/mean where extreme highs and lows are not counted as heavily. The initial value from the first pass is used in both acid and non-acid reflux types, and it is then changed adaptively as a new episode is observed.

The gastric contents impedance is not constant over the study period and it increases especially after meals, and the adaptive algorithm is used to keep up with rate of change of gastric content impedance $Z_c$ according to:

$$Z_{cTnew} = Z_{cTold} \pm \epsilon \|Z_{cTold} - Z_{min}\|^2 \tag{8}$$

Figure 9:
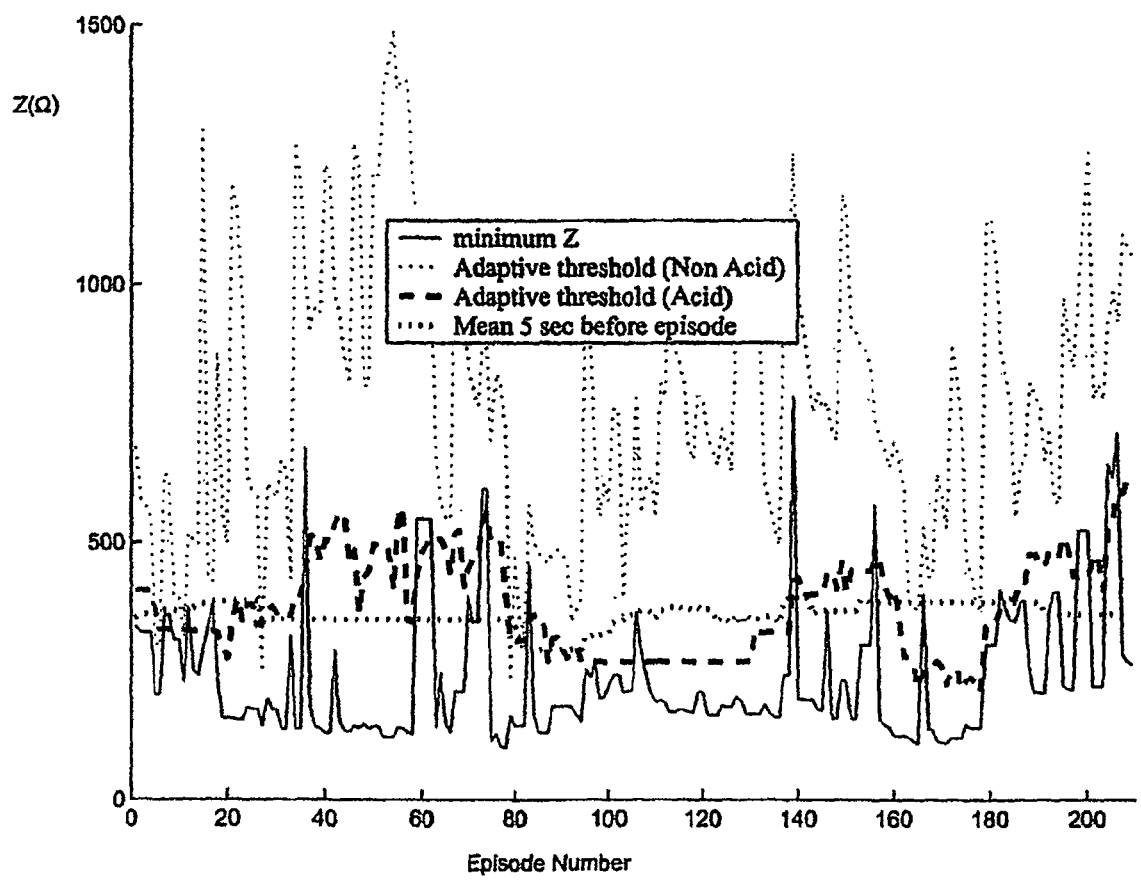
FIG. 9 is a graph illustrating example adaptively changing gastric content thresholds corresponding to acid reflux episodes and non-acid reflux episodes.

FIG. 9 shows the minimum impedance $Z_{min}$ reached in CH6 (distal) during each episode along with the adaptively changing threshold $Z_{cTnew}$ on the gastric content impedance. Two thresholds were used, one corresponds to acid reflux episodes and the other corresponds to non-acid reflux episodes. The pre-episode baseline impedance is also shown in FIG. 9, which is a mean five (5) seconds before the episode.

As mentioned above, whenever the value of the patient impedance $Z_p$ as well as the change in impedance during gastrointestinal tract events are also low, these are termed as "low baseline" waveforms. The analysis of low-baseline waveforms is more challenging since there is a smaller dynamic range for signal variations. The analysis in this case starts by applying an adaptive filter to the smooth version of an impedance waveform, preferably a mid-channel waveform, such as CH4. The primary input $d_k$ for the filter is a delayed sequence of the smooth signal $X_k$. The weight vector of the filter is obtained from Widrow-Hoff least mean square (LMS) algorithm $$W_{k+1} = W_k - 2\mu(d_k - y_k)X_k \tag{9}$$

where $y_k$ is the output and $\mu$ is a factor that controls stability and convergence. If the filtered signal at any local maxima of the details exhibits impedance transition to the gastric contents impedance level, then there will be a candidate episode and the previously mentioned conditions are evaluated to make a firm decision regarding the episode.

In low baseline waveforms, the analysis described above is initiated from the mid-channel waveforms, e.g., CH4, observations. Similarly, the pH observations can also be used to initiate the analysis by observing the propagation starting with the pH channel. If pH drops below a threshold, then the propagation direction and the conditions described above for normal and semi-normal impedance signals are used to determine the presence of gastrointestinal tract events. As mentioned above, in addition to the processes described above, to determine candidate episodes or events other evaluations, such as neural networks can be used, if desired, to further evaluate the candidate episodes in view of normalized example episodes identified by experts in the field as being representative of certain kinds of episodes. In the example 150 of FIG. 7, there are three neural networks developed for various aspects of that function. Each of the neural networks has a specific task, i.e., gas episodes detection, episodes of large impedance changes detection, and assimilate the statistics obtained from all stages to further refine the classification of episodes.

Figure 10:
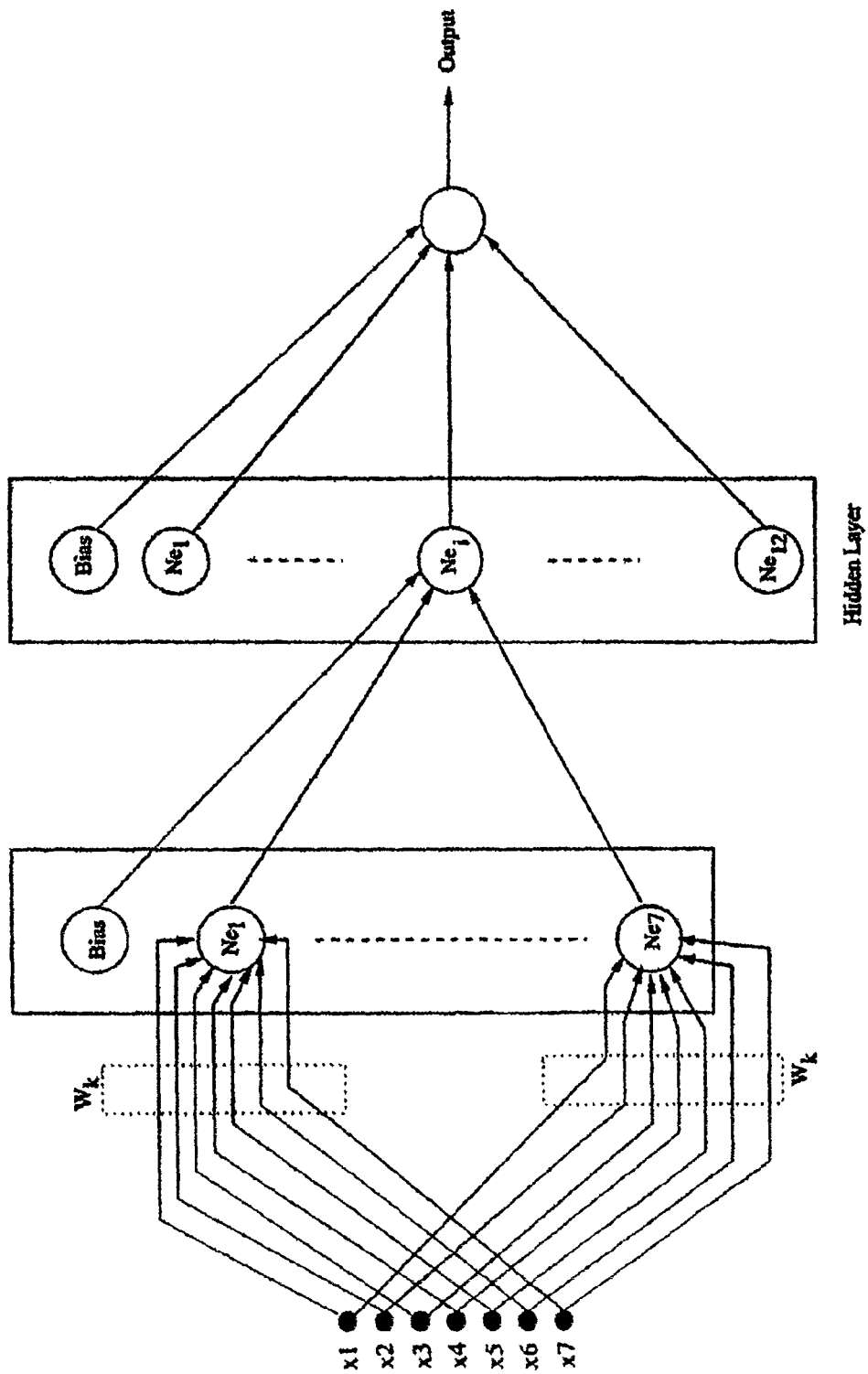
FIG. 10 is a schematic diagram of an example neural network that can be used, if desired, to compare results of the process of this invention with examples of various waveforms for further characterization.

Since the idea of the three neural networks are similar, the third neural network will be described in detail as an example. The positive predictive value of the detection process was found to be low when the data contain episodes of a liquid type. Most of the time these false positive episodes are due to closely located swallows. In order to enhance the positive predictive value and maintain the sensitivity, a neural network is introduced as an extra step that is used when the reflux episode is of a liquid type. After studying the characteristics of the false positive episode, a neural network shown in FIG. 10 with the following parameters extracted from the impedance measurements on all of the impedance channels CH1, CH2, CH3, CH4, CH5, CH6 was applied to reject the false positive episodes:

$x_1$: Ratio of a one-second impedance mean after the minimum value is reached to a 2-second mean starting 3 seconds before the start of the episode in CH1.

$x_2$: Ratio of a one-second impedance mean after the minimum value is reached to a 2-second mean starting 3 seconds before the start of the episode in CH2.

$x_3$: Minimum value reached in CH6 a few seconds after the episode (max 4 sec).

$x_4$: Minimum value reached in CH5 few seconds after the episode (max 4 sec).

$x_5$: Ratio of a one-second impedance mean after the minimum value is reached to a 2-second mean starting 3 seconds before the start of the episode CH3.

$x_6$: Ratio of a one-second impedance mean after the minimum value is reached to a 2-second mean starting 3 seconds before the start of the episode in CH4.

$x_7$: Ratio of a minimum pH reached after the episode to a one-second pre-episode mean.

These intervals above and other parameters may vary and can be tuned for channel spacing and sensitivity as desired.

The activation function used in the neurons simulates a tan-sigmoid with a range of [−1, 1]. The following activation function is used:

$$f(x) = \frac{2.0}{1 + e^{-2x}} - 1 \tag{10}$$

Delta rule is employed in the training process of the neural network. The algorithm can be described as follows:

Start with epoch i, propagate the input $x_k$ through the network and compute the output $y_k$.

Compute weights and biases correction terms as follows:
Output layer weights:

$$\delta W_0 = \alpha(T - y)xf'(Y_h) \tag{11}$$

where $f'(x) = \dfrac{4e^{-2x}}{(1+e^{-2x})^2}$, $T$ is the target given by $$T = \begin{cases} 1 & \text{if episode is true;} \\ -1 & \text{if episode is not} \end{cases} \tag{12}$$

and $Y_i$ is the output of the hidden layer.
Hidden layer weights:

$$\delta W_0 = \alpha(T-y)xf'(Y_i) \tag{13}$$

where $Y_h$ is the output of the hidden layer.

Input layer weights:

$$\delta W_i = \alpha(T-y)xf'(X_k) \quad (14)$$

Update the weights and the biases.

Figure 11:
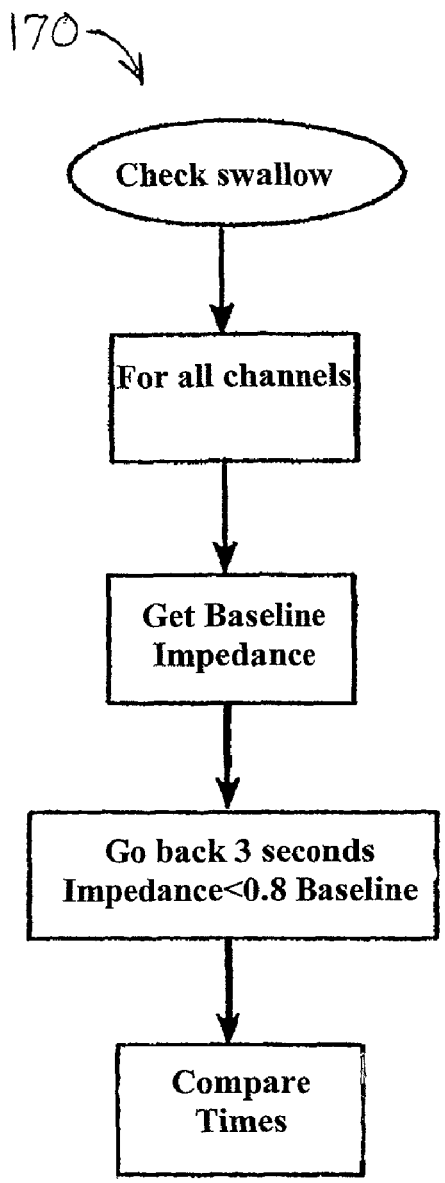
FIG. 11 illustrates a procedure to check whether a possible episode might be a swallow.
Figure 12:
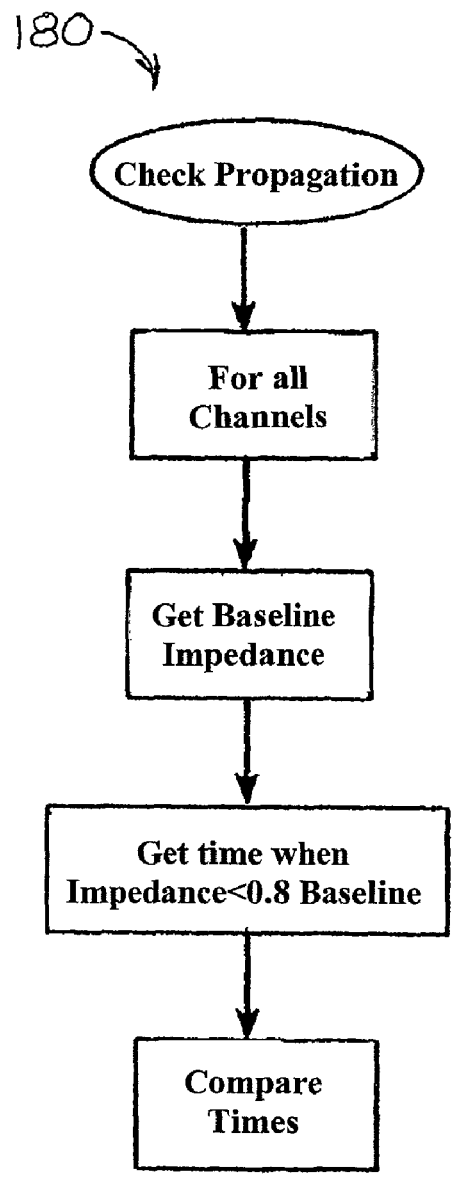
FIG. 12 illustrates a procedure to check propagation direction.

As mentioned above in relation to FIG. 7, two checks can be made in an attempt to reduce false positives and thereby increase the accuracy and dependability of the system. These two checks, as shown in FIG. 7, include a check for swallow 170 and a check for propagation direction 180. These checks are explained in more detail in FIGS. 11 and 12.

Essentially, the swallow check 170 in this example retrieves the baseline impedance for all channels for the episode, goes back in time, e.g., three seconds, and, from the times when the impedance in each of the waveforms back in such time is less than 0.8 times the baseline impedance comparing those times to make sure that the propagation is not a result of a pre-episode swallow. The propagation check comprises getting the baseline impedance for all the channels for the episode, getting the time when the impedance of each channel is less than 0.8 times the baseline impedance, and comparing those times to be sure that the propagation direction of the inverse pulse shape is from the distal to the proximal.

The waveforms particular to a specific embodiment are dependent on many factors, including the overall design, shape, and manufacturing particularities of the catheter, dynamic range and sensitivity of the data collection device, physiology of the patient, ambient noise, and a host of other factors. A variable that is used to characterize a waveform is specific to the particular set up of catheter and data collection device and may not have any meaning for data from a different apparatus. For example, a particular design of a catheter and data collection device may have a waveform with characteristic peaks and valleys that are common to reflux events whereas a different catheter may have different waveform outputs. Thus, the use of a particular characteristic variable, such as the ratio using the mean for a certain time after the minima prior to the transition point may have meaningless results if such a minima were not typically present. Persons skilled in the art of waveform analysis will be capable of determining the characteristics appropriate for their particular applications.

Various combinations of minima, maxima, averages, variances, or other mathematical representation may be used by those skilled in the art to classify various events. The values produced by the classification may be passed to a neural network for evaluation. The particular values selected can depend on the data being analyzed, the probe locations, particular diseases to diagnose, any smoothing or data transformations, method for selecting entry points and exit points, and other factors. Those skilled in the art of data analysis may use many different methods while keeping within the scope and intent of the present invention.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. The words "comprise", "comprises", "comprising", "include", "including", and "includes" when used in this specification are intended to specify the presence of stated features, integers, components, or steps, but they do not preclude the presence or addition of one or more other features, integers, components, steps, or groups thereof. It is intended that the appended claims be construed to include other alternative embodiments of the invention except insofar as limited by the prior art.

What is claimed is:

1. A method of identifying and classifying reflux episodes in a plurality of impedance versus time waveforms obtained simultaneously at a plurality of different locations spaced apart from each other along a length of an esophagus between the pharynx and the stomach along with a pH versus time curve obtained in the esophagus, wherein the impedance versus time waveforms include proximal waveforms from the locations closest to the pharynx, distal waveforms from the locations closest to the stomach, and mid-channel waveforms between the proximal waveforms and the distal waveforms, said method comprising:

applying a smoothing algorithm to the impedance versus time waveforms;

locating candidate transition points and candidate end points in the smoothed waveforms to indicate candidate reflux episodes;

determining whether a pH drop occurs in the pH versus time curve contemporaneous with a candidate transition point to thereby indicate whether the candidate reflux episode associated with such candidate transition point is acidic or non-acidic;

determining a gastric contents impedance threshold for acid reflux episodes;

determining a gastric contents impedance threshold for non-acid reflux episodes;

determining if there is impedance of acid gastric contents associated with the candidate acid reflux episodes by comparing values associated with impedance at the candidate transition points for candidate acid reflux episodes to the gastric contents impedance threshold for acid reflux episodes;

determining if there is impedance of non-acid gastric contents associated with the candidate non-acid reflux episodes by comparing values associated with impedance at the candidate transition points for candidate non-acid reflux episodes to the gastric contents impedance threshold for non-acid reflux episodes;

for candidate acid reflux episodes wherein there is impedance of acid gastric contents, determining if there is a propagation direction of corresponding candidate transition points in any of the other impedance versus time waveforms starting from a distal waveform;

for candidate non-acid reflux episodes wherein there is impedance of non-acid gastric contents, determining if there is a propagation direction of corresponding candidate transition points in any of the other impedance versus time waveforms starting from a distal waveform;

classifying candidate acid reflux episodes as actual acid reflux episodes based at least in part on determination that there is impedance of acid gastric contents and on determination that there is propagation direction; and classifying candidate non-acid reflux episodes as actual non-acid reflux episodes based at least in part on determination that there is impedance of non-acid gastric contents and on determination that there is propagation direction.

2. The method of claim 1 including, for candidate acid reflux episodes wherein there is impedance of acid gastric contents, determining if there is a propagation direction of corresponding candidate transition points in any of the other impedance versus time waveforms starting from the most distal impedance versus time waveform.

3. The method of claim 1, including, for candidate non-acid reflux episodes wherein there is impedance of non-acid gastric contents, determining if there is a propagation direction of corresponding candidate transition points in any of the other impedance versus time waveforms starting from the most distal impedance versus time waveform.

4. The method of claim 1, including determining the initial propagation direction from a series of times at which transition points to impedance of gastric content occur in the distal waveforms starting with the most distal waveform.

5. The method of claim 1, including determining the initial propagation direction from a series of times at which transition points to impedance of gastric content occur in the distal waveforms starting with the most distal waveform, and in the mid-channel waveforms and proximal waveforms.

6. The method of claim 1, including determining the initial propagation direction from a series of times at which transition points to impedance of non-acid gastric content occur in the distal waveforms starting with the most distal waveform.

7. The method of claim 1, including determining the initial propagation direction from a series of times at which transition points to impedance of non-acid gastric content occur in the distal waveforms, starting with the most distal waveform, and in the mid-channel waveforms and proximal waveforms.

8. The method of claim 1, including determining the gastric contents impedance threshold for acid reflux episodes at least in part by impedance value that occurs contemporaneous with the pH drop.

9. The method of claim 1, including determining the gastric contents impedance threshold for acid reflux episodes by an impedance value that occurs contemporaneous with candidate acid reflux episodes over time.

10. The method of claim 1, including determining the gastric contents impedance threshold for non-acid reflux episodes by an impedance value that occurs contemporaneous with candidate non-acid reflux episodes over time.

11. The method of claim 1, including:
determining whether the impedance versus time waveforms exhibit either: (i) normal baseline impedance levels that are indicative of conductivity of healthy esophageal tissue; or (ii) abnormally low baseline impedance levels that are indicative of conductivity of diseased esophageal tissue, which is lower than the conductivity of healthy esophageal tissue;
determining whether the change in impedance during gastrointestinal tract events are either: (i) large as indicated by the mean distribution of minimum to baseline impedance being less than or equal to 0.5; or (ii) low as indicated by the mean distribution of minimum to baseline impedance being greater than 0.5 and less than or equal to 0.8; and
if the impedance versus time waveforms exhibit abnormal low baseline impedance levels and the change in impedance during gastrointestinal tract events are low, then applying an adaptive filter to the smooth version of at least one of the impedance versus time waveforms before determining if there is impedance of either acid or non-acid gastric contents.

12. The method of claim 11, including distinguishing candidate gas reflux episodes from candidate liquid episodes based on instantaneous increases in impedance over the baseline impedance in distal, mid-channel, and proximal waveforms.

13. The method of claim 1, including applying neural network processing to candidate liquid refluxes to reject false positive indications of liquid refluxes based on input parameters selected from a group consisting of:
(i) ratio of a post-time impedance mean after a minimum impedance value is reached to a pre-time impedance mean before start of the episode in one proximal waveform;
(ii) ratio of a post-time impedance mean after a minimum impedance value is reached to a pre-time impedance mean before start of the episode in another proximal waveform;
(iii) minimum impedance value reached in one distal waveform at a time after the episode;
(iv) minimum impedance value reached in another distal waveform at a time after the episode;
(v) ratio of a post-time impedance mean after a minimum impedance value is reached to a pre-time impedance mean before start of the episode in one mid-channel waveform;
(vi) ratio of a post-time impedance mean after a minimum impedance value is reached to a pre-time impedance mean before the start of the episode in another mid-channel waveform; and
(vii) ratio of a minimum pH reached after the episode to a pre-episode pH mean.

14. The method of claim 13, wherein:
(i) for the one proximal waveform, the post-time is one second, and the pre-time is two seconds starting three seconds before the start of the episode;
(ii) for the another proximal waveform, the post-time is one second, and the pre-time is two seconds starting three seconds before the start of the episode;
(iii) for the one distal waveform, the time is not more than four seconds;
(iv) for the another distal waveform, the time is not more than four seconds;
(v) for the one mid-channel waveform, the pre-time is two seconds starting three seconds before the start of the episode;
(vi) for the another mid-channel waveform, the pre-time is two seconds starting three seconds before the start of the episode; and
(vii) for the pre-episode mean in the pH ratio is one-second pre-episode.

15. The method of claim 13, including checking for indication of swallow episode instead of reflux episode by, for each distal, mid-channel and proximal waveform, going back a distinct time from the candidate episode to get times when the impedance is less than a distinct fraction of the baseline impedance in that waveform, and comparing those times for indication of a pre-episode swallow propagation during such distinct time before the episode.

16. The method of claim 15, wherein the distinct time is three seconds.

17. The method of claim 15, wherein the distinct fraction is 0.8.

18. The method of claim 13, including checking for propagation by, for each distal, mid-channel, and proximal waveform, determining the time when the impedance during the candidate episode is a distinct fraction of the baseline impedance, and comparing those times to verify propagation of the candidate episode is from distal to proximal.

19. The method of claim 18, wherein the distinct fraction is 0.8.

20. A method of identifying and classifying reflux episodes in a plurality of impedance versus time waveforms obtained simultaneously at a plurality of different locations spaced apart from each other along a length of an esophagus between the pharynx and the stomach along with a pH versus time curve obtained in the esophagus, wherein the impedance versus time waveforms include proximal waveforms from the locations closest to the pharynx, distal waveforms from locations closest to the stomach, and mid-channel waveforms between the proximal waveforms and the distal waveforms, said method comprising:

performing wavelet transformation to the impedance versus time waveforms to obtain smoothed curves of the impedance versus time waveforms and detail curves showing local positive and negative maxima peaks corresponding to positive and negative slopes in the smoothed impedance versus time waveforms;

determining whether the smoothed impedance versus time waveforms exhibit either normal baseline impedance levels that are characteristic of conductivity of healthy esophageal tissue or low baseline impedance levels that are characteristic of conductivity of diseased esophageal tissue;

determining whether change in impedance in the smoothed impedance versus time waveforms during gastrointestinal tract events are either: (i) large as indicated by the mean distribution of minimum to baseline impedance levels being not greater than a mean distribution value; or (ii) low as indicated by the mean distribution of minimum to baseline impedance levels being greater than a mean distribution value;

if the smoothed impedance versus time waveforms exhibit low baseline levels and the change in impedance during gastrointestinal tract events are low, then applying an adaptive filter to at least one of the smoothed impedance versus time waveforms with a primary input for the adaptive filter being a delayed sequence of the said at least one smoothed impedance versus time waveform and determining a candidate episode by transition of impedance level in the adaptive filter output to a gastric contents impedance level; and if either the smoothed impedance versus time waveforms do not exhibit low baseline levels or the change in impedance during gastrointestinal tract events are not low, then determining a candidate episode by transition of impedance level in the smoothed waveforms to a gastric contents impedance level.

21. The method of claim 20, wherein the mean distribution value is 0.5.

22. The method of claim 20, wherein the adaptive filter is applied to at least one mid-channel waveform.

23. The method of claim 20, wherein the gastric contents impedance level is an acid gastric contents impedance level.

24. The method of claim 20, wherein the gastric contents impedance level is a non-acid gastric contents impedance level.

25. The method of claim 23, including determining that the gastric contents impedance level is an acid gastric contents impedance level by occurrence of a pH drop contemporaneous with a local maxima that corresponds to occurrence of a candidate episode.

26. The method of claim 24, including determining that the gastric contents impedance level is a non-acid gastric contents impedance level by absence of a pH drop contemporaneous with a local maxima that corresponds to occurrence of a candidate episode.

* * * * *